US011636178B2

(12) United States Patent
Park

(10) Patent No.: US 11,636,178 B2
(45) Date of Patent: Apr. 25, 2023

(54) ELECTRONIC DEVICE FOR PROVIDING ACTIVITY INFORMATION ABOUT USER AND METHOD OF OPERATING THE SAME

(71) Applicant: Samsung Electronics Co., Ltd., Gyeonggi-do (KR)

(72) Inventor: Kwansu Park, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 217 days.

(21) Appl. No.: 17/084,793

(22) Filed: Oct. 30, 2020

(65) Prior Publication Data

US 2021/0134469 A1    May 6, 2021

(30) Foreign Application Priority Data

Oct. 30, 2019 (KR) .................... 10-2019-0136696

(51) Int. Cl.
*G06K 9/62* (2022.01)
*G16Y 20/40* (2020.01)
(Continued)

(52) U.S. Cl.
CPC .......... *G06F 18/2321* (2023.01); *G16Y 20/40* (2020.01); *G16Y 40/10* (2020.01);
(Continued)

(58) Field of Classification Search
None
See application file for complete search history.

(56) References Cited

U.S. PATENT DOCUMENTS 8,769,676 B1 * 7/2014 Kashyap ............... G06F 21/554
726/22
2015/0182843 A1 * 7/2015 Esposito ............ G06K 9/00496
700/91

(Continued)

FOREIGN PATENT DOCUMENTS

KR          20100096564 A   *  9/2010
KR     10-2020-0056197 A      5/2020
WO      WO-2020149454 A1  *  7/2020 ............. G06F 16/27

Primary Examiner — Mohamed A. Wasel
Assistant Examiner — Mohammad Yousuf A. Mian
(74) Attorney, Agent, or Firm — Cha & Reiter, LLC

(57) ABSTRACT

According to certain embodiments, an electronic device comprises a communication module; a plurality of sensors and configured to obtain sensing data; at least one processor operatively connected to the plurality of sensors and the communication module; and a memory operatively connected to the at least one processor, wherein the memory stores instructions that, when executed, cause the at least one processor to perform a plurality of operations comprising: transmitting the sensing data to a server through the communication module; receiving, from the server, information on a similarity between the sensing data and a first cluster among a plurality of clusters clustering data related to user activities, through the communication module, wherein the similarity is identified based on a center similarity score between the sensing data and the first cluster, a score that is a function of a variance of the first cluster, a score that is a function a distance between the first cluster and other clusters, and an intersection score between the first cluster and a second cluster adjacent to the first cluster; and executing a function corresponding to the sensing data based on the similarity.

15 Claims, 24 Drawing Sheets

(51) Int. Cl.
*G16Y 40/10* (2020.01)
*G16Y 40/20* (2020.01)
*H04L 43/04* (2022.01)
*H04L 67/12* (2022.01)
*G06F 18/2321* (2023.01)

(52) U.S. Cl.
CPC .............. *G16Y 40/20* (2020.01); *H04L 43/04* (2013.01); *H04L 67/12* (2013.01)

(56) References Cited

U.S. PATENT DOCUMENTS

| | | | | |
|---|---|---|---|---|
| 2016/0151668 | A1* | 6/2016 | Barnes | G09B 7/02 706/46 |
| 2017/0358434 | A1* | 12/2017 | Matsuura | G01N 31/00 |

* cited by examiner

| Property | Field name | Description |
|---|---|---|
| Session info | ActivitySessionId | Activity Session ID |
| | ActivityType | Activity Type |
| | PacketId | Activity data packet id |
| | Time | Session Generation Time |
| | Duration | Activity Duration |
| | Temperature | Temperature |
| | Humidity | Humidity |
| Physical metrics | Speed | Speed |
| | Distance | Distance |
| | Calorie | Consumed Calories |
| | StepCount | Number of Steps |
| | Altitude | Altitude |
| | Ascent | Uphill |
| | Descent | Downhill |
| Biometrics | HeartRate | Number of Heart Beats |
| | SpO2 | Oxygen Saturation |
| Geographic metrics | Latitude | Latitude |
| | Longitude | Longitude |
| User information | UserInfoAge | User Age |
| | UserInfoWeight | User Weight |
| | UserHeight | User Height |

FIG.3B

|   | DISTANCE | STEP COUNT | SPEED | CALORIES | HEART RATE |
|---|---|---|---|---|---|
| 1 | 20.310 | 27 | 1.416667 | 1.070 | 93 |
| 2 | 1.684 | 2 | 2.170212 | 0.140 | 93 |
| 3 | 85.718 | 105 | 1.965329 | 5.550 | 76 |
| 4 | 80.684 | 104 | 1.591258 | 4.029 | 82 |
| 5 | 10.450 | 16 | 1.138889 | 0.540 | 67 |
| 6 | 84.830 | 106 | 1.666667 | 4.050 | 75 |
| ⋮ | ⋮ | ⋮ | ⋮ | ⋮ | ⋮ |

FIG.3C

| | CLOSEST CLUSTER | WS | BS | CENTER SS | IS | TS |
|---|---|---|---|---|---|---|
| A1 | A | 0.72 | 8.62 | 0.92 | 0 | 3.18 |
| A2 | B | 0.63 | 4.98 | 0.83 | 2.21 | 1.35 |
| A3 | C | 0.52 | 5.23 | 0.88 | 2.21 | 1.36 |
| A4 | C | 0.52 | 5.23 | 0.72 | 2.21 | 1.39 |
| A5 | A | 0.72 | 8.62 | 0.38 | 0 | 4.95 |

ELECTRONIC DEVICE FOR PROVIDING ACTIVITY INFORMATION ABOUT USER AND METHOD OF OPERATING THE SAME

CROSS-REFERENCE TO RELATED APPLICATION(S)

This application is based on and claims priority under 35 U.S.C. § 119 to Korean Patent Application No. 10-2019-0136696, filed on Oct. 30, 2019, in the Korean Intellectual Property Office, the disclosure of which is incorporated by reference herein in its entirety.

BACKGROUND

Field

The disclosure relates to an electronic device for providing information about a user activity and a method of operating the same.

Description of Related Art

In recent years, electronic devices such as smart phones are capable of executing various functions. The electronic device can collect a variety of data about the user regarding user activity. The volume of data has increased quite rapidly. It is thus important to be able to verify the accuracy of large volumes of data in an efficient manner.

SUMMARY

According to certain embodiments, an electronic device comprises a communication module; a plurality of sensors and configured to obtain sensing data; at least one processor operatively connected to the plurality of sensors and the communication module; and a memory operatively connected to the at least one processor, wherein the memory stores instructions that, when executed, cause the at least one processor to perform a plurality of operations comprising: transmitting the sensing data to a server through the communication module; receiving, from the server, information on a similarity between the sensing data and a first cluster among a plurality of clusters clustering data related to user activities, through the communication module, wherein the similarity is identified based on a center similarity score between the sensing data and the first cluster, a score that is a function of a variance of the first cluster, a score that is a function a distance between the first cluster and other clusters, and an intersection score between the first cluster and a second cluster adjacent to the first cluster; and executing a function corresponding to the sensing data based on the similarity.

According to certain embodiments, an electronic device comprises: a plurality of sensors; at least one processor operatively connected to the plurality of sensors; and a memory operatively connected to the at least one processor and configured to store information about a plurality of clusters obtained by clustering data related to user activities, wherein the memory stores instructions which, when executed, cause the at least one processor to perform a plurality of operations comprising: obtaining sensing data through the sensor module; identifying a similarity between the sensing data and a first cluster among the plurality of clusters, wherein the similarity is identified based on a center similarity score between the sensing data and the first cluster, a score that is a function of a variance of the first cluster, a score that is a function of a measure of a distance between the first cluster and a second cluster adjacent to the first cluster, and an intersection score between the first cluster and the second cluster; and executing a function corresponding to the sensing data based on the similarity.

According to certain embodiments, an electronic device comprises a plurality of sensors; at least one processor operatively connected to the sensor module; and a memory operatively connected to the processor, wherein the memory stores instructions which, when executed, cause the at least one processor to perform a plurality of operations comprising: obtaining a plurality of sensing data through the plurality of sensors; identifying activity information based on first sensing data among the of sensing data, wherein the other sensing data except for the first sensing data is not used to identify the activity information; identifying a similarity between the sensing data and a plurality of clusters related to the sensing data; and identifying a reliability of the activity information based on the similarity.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 3A, 3B and 3C are diagrams illustrating an operation of clustering a plurality of data by a server according to certain embodiments;

DETAILED DESCRIPTION

For example, an electronic device may include various sensors for detecting a user's motion or sensing biometric information about a user. The electronic device may sense a user activity in real time through various sensors and store the sensed data. The electronic device may also record data about the user activity in real time and utilize the recorded data.

It would be problematic if data about the user activity collected by the electronic device is used for various functions or services provided by the electronic device without a separate verification procedure. Reliability. This may give rise to provisioning of an incorrect or erroneous service to the user.

As the performance of electronic devices has improved along with the development of data analysis technology, large-scale data analysis has become possible. Large volumes of information exist in user activity data, and as the information is accumulated, data representing unique characteristics of the user may be extracted through machine learning.

Provided is an electronic device for solving reliability verifying newly obtained user activity data by comparing a plurality of clusters obtained by clustering existing user activity data with the newly obtained user activity data, and a method of operating the electronic device.

Provide is also an electronic device for enabling provision of state-of-the art healthcare services, and a method of operating the same.

Additional aspects will be set forth in part in the description which follows and, in part, will be apparent from the description, or may be learned by practice of the presented embodiments of the disclosure.

Figure 1:
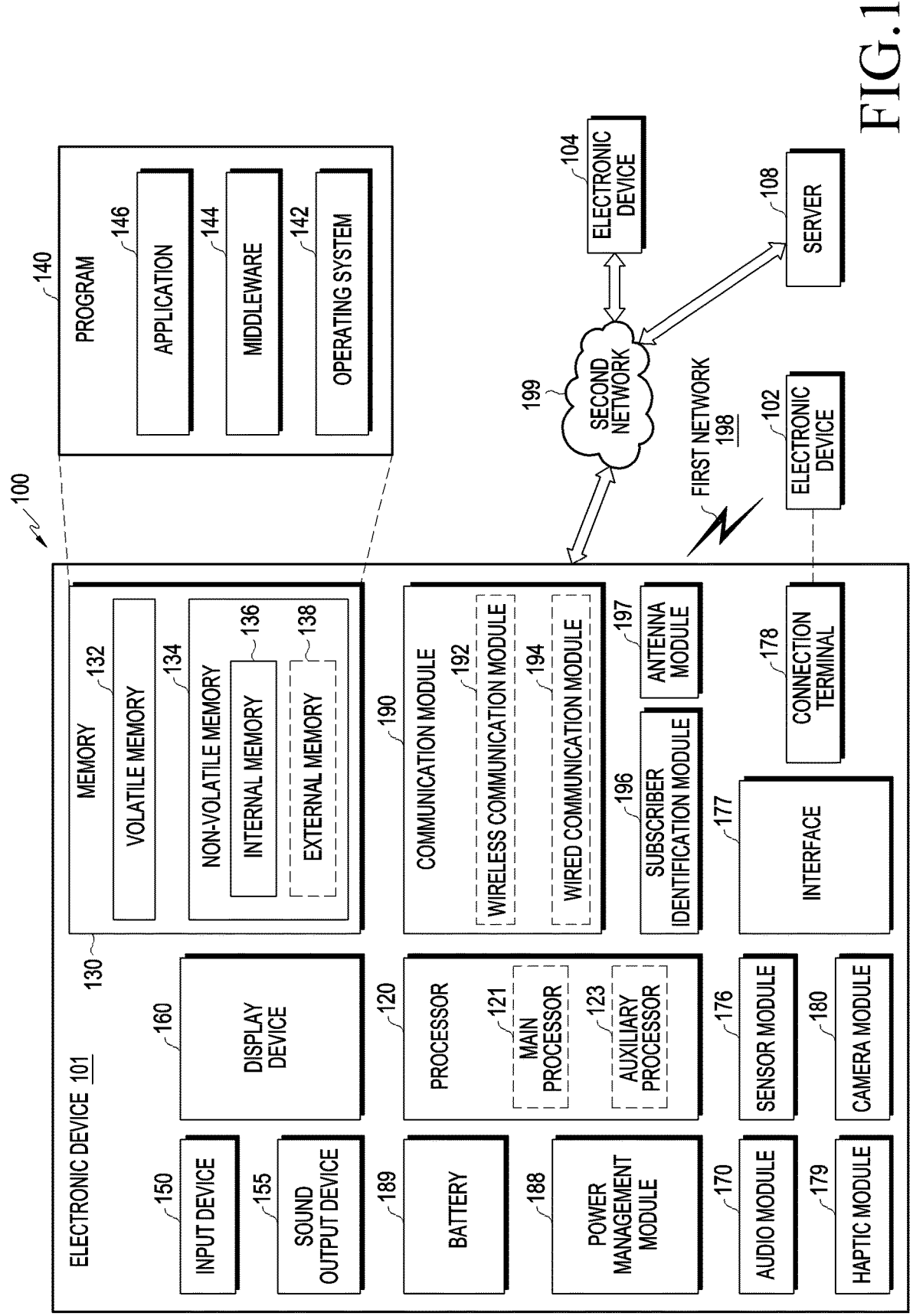
FIG. 1 is a block diagram illustrating an electronic device in a network environment according to certain embodiments.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (MI) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, and/or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a principal processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the principal processor 121. Additionally or alternatively, the auxiliary processor 123 may be adapted to consume less power than the principal processor 121, or to be specific to a specified function. The auxiliary processor 123 may be implemented as separate from, or as part of the principal processor 121.

The auxiliary processor 123 may control at least some of functions or states related to at least one component (e.g., the display device 160, the sensor module 176, or the communication module 190) among the components of the electronic device 101, instead of the principal processor 121 while the principal processor 121 is in an inactive (e.g., sleep) state, or together with the principal processor 121 while the principal processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

Figure 2:
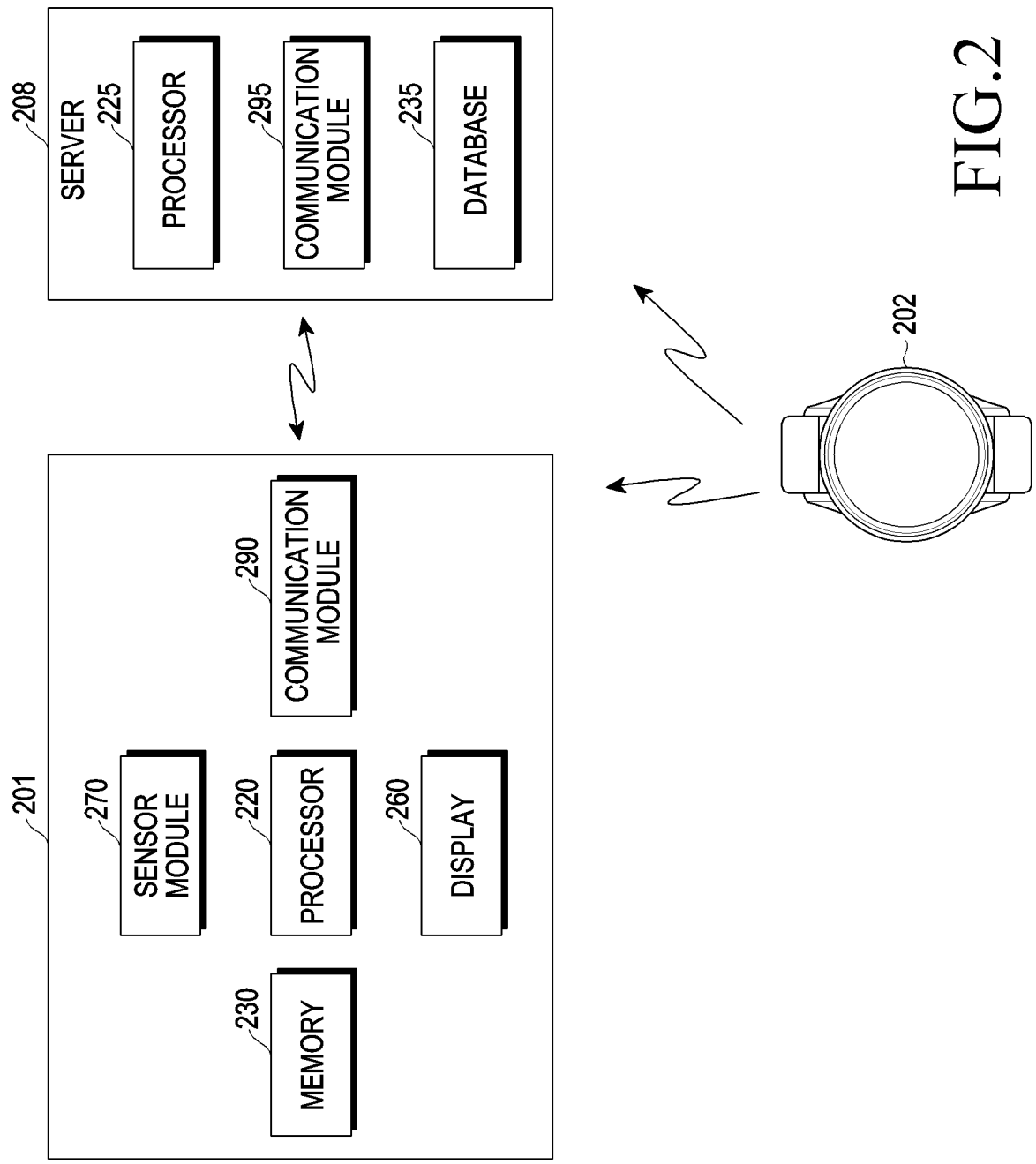
FIG. 2 is a schematic block diagram illustrating an electronic system according to certain embodiments.

FIG. 2 is a schematic block diagram illustrating an electronic system according to certain embodiments.

Referring to FIG. 2, the electronic system may be identical or similar to the network environment 100 illustrated in FIG. 1. For example, a first electronic device 201 may be identical or similar to the electronic device 101 illustrated in FIG. 1. A second electronic device 202 may be identical or similar to the electronic device 102 illustrated in FIG. 1. Further, a server 208 may be identical or similar to the server 108 illustrated in FIG. 1.

The first electronic device 201 may include a processor 220, a memory 230, a display 260, a sensor module 270, and a communication module 290. The term processor 220 shall be understood to refer to both the singular context and the plural context.

The processor 220 may receive sensing data obtained through the sensor module 270. The processor 220 may store the sensing data in the memory 230. Further, the processor 220 may transmit the sensing data to an external electronic device (for example, the server 208 or another electronic device) through the communication module 290. For example, the sensing data may be data obtained through the sensor module 270. Further, the sensing data may include data related to a user activity.

The processor 220 may provide overall control to the operations of the first electronic device 201.

The processor 220 may identify whether the sensing data has features similar to features common in data related to user activities. For example, the processor 220 may identify similarity values representing the degrees of similarity between the features of the sensing data and the common features of the data related to the user activities. For example, the processor 220 may receive the similarity values from the server 208. Alternatively, the processor 220 may autonomously measure and identify the similarity values. In this case, the processor 220 may obtain cluster information representing the common features of the data related to the user activities from the server 208, and measure and identify the similarity values by using the cluster information. Alternatively, the processor 220 may obtain cluster information representing the common features of the data related to the user activities by autonomously clustering the data related to the user activities.

The processor 220 may cluster data related to the user activities stored in the memory 230 to identify the common features of the data related to the user activities, and obtain information (that is, cluster information) about a plurality of clusters representing the common features of the data related to the user activities. For example, the processor 220 may update the information about the plurality of clusters at predetermined intervals. Further, when the processor 220 obtains sensing data from the sensor module 270 or receives sensing data from the second electronic device 202, the processor 220 may update the information about the plurality of clusters.

The processor 220 may disregard sensing data that is deemed to have low reliability, or prevent execution of a function from being performed on data deemed to have low reliability. The processor 220 may identify a similarity value of the sensing data and execute a function corresponding to the sensing data according to the identification result. For example, the processor 220 may determine the reliability of the sensing data based on the similarity value of the sensing data. The processor 220 may execute a function related to the sensing data based on the determined reliability. For example, the reliability may be a value corresponding to the similarity value. For example, when the similarity value is high, the reliability may be high, and when the similarity value is low, the reliability may be low. On the contrary, when the similarity value is low, the reliability may be high, and when the similarity value is high, the reliability may be low.

The memory 230 may store data of the first electronic device 201. For example, the memory 230 may store data related to user activities. Further, the memory 230 may store sensing data obtained through the sensor module 270.

The display 260 may display information related to an operation or function of the first electronic device 201. For example, the display 260 may display information related to sensing data under the control of the processor 220.

The sensor module 270 may include a plurality of sensors. For example, the plurality of sensors may include sensors capable of sensing user activities (a gyro sensor, an accelerometer sensor, a gravity sensor, a gesture sensor, a grip sensor, a proximity sensor, among others), sensors capable of sensing a user's biometric information (a fingerprint sensor, an iris sensor, a photoplethysmographic (PPG) sensor, an image sensor, and so on), and sensors capable of sensing the user's location or surroundings (a global positioning system (GPS) sensor, an illuminance sensor, a temperature sensor, a humidity sensor, and so on).

The second electronic device 202 may include at least one sensor. The second electronic device 202 may transmit data sensed by the at least one sensor to the first electronic device 201 and/or the server 208. Further, the second electronic device 202 may store the data sensed by the at least one sensor. For example, the second electronic device 220 may include a wearable device. While the second electronic device 220 is shown in FIG. 2 as a smart watch, the technical idea of the present disclosure may not be limited thereto.

The server 208 may include a processor 225, a database 235, and a communication module 295.

The processor 225 may provide overall control to the operations of the server 208.

The processor 225 may store sensing data received from the first electronic device 201 and the second electronic device 202 in the database 235. That is, the processor 225 may store data (or sensing data) related to user activities in the database 235. In addition to the sensing data, the processor 225 may also include information about a user of the first electronic device 201 or a user of the second electronic device 202 (for example, information about the age, gender, height, weight, and medical history of the user) in the database 235.

According to certain embodiments, the processor 225 may obtain cluster information representing features common in data related to the user activities. For example, the processor 225 may cluster the data related to the user activities stored in the database 235, and obtain information about a plurality of clusters representing the common features of the data related to the user activities (that is, cluster information). For example, the processor 225 may update the information about the plurality of clusters at predetermined intervals. Further, the processor 225 may update the information about the plurality of clusters, when receiving sensing data from the first electronic device 201 and/or the second electronic device 202. Alternatively, processor 220 may perform the foregoing locally.

The processor 225 may identify similarity values by comparing the sensing data received from the first electronic device 201 and/or the second electronic device 202 with the plurality of clusters. The processor 225 may further transmit the similarity values to the first electronic device 201 through the communication module 295. Alternatively, processor 220 may perform the foregoing locally.

According to certain embodiments, the processor 225 may transmit the information about the plurality of clusters, that is, the cluster information through the communication module 295. In this case, the first electronic device 201 may identify a similarity value of sensing data by using the cluster information. Alternatively, processor 220 may perform the foregoing locally.

While the server 208 is shown in FIG. 2 as including the database 235, the database 235 may be configured as a separate device from the server 208. In certain embodiments, the functions of the server 208 may be integrated with the first electronic device 201.

Figure 3A:
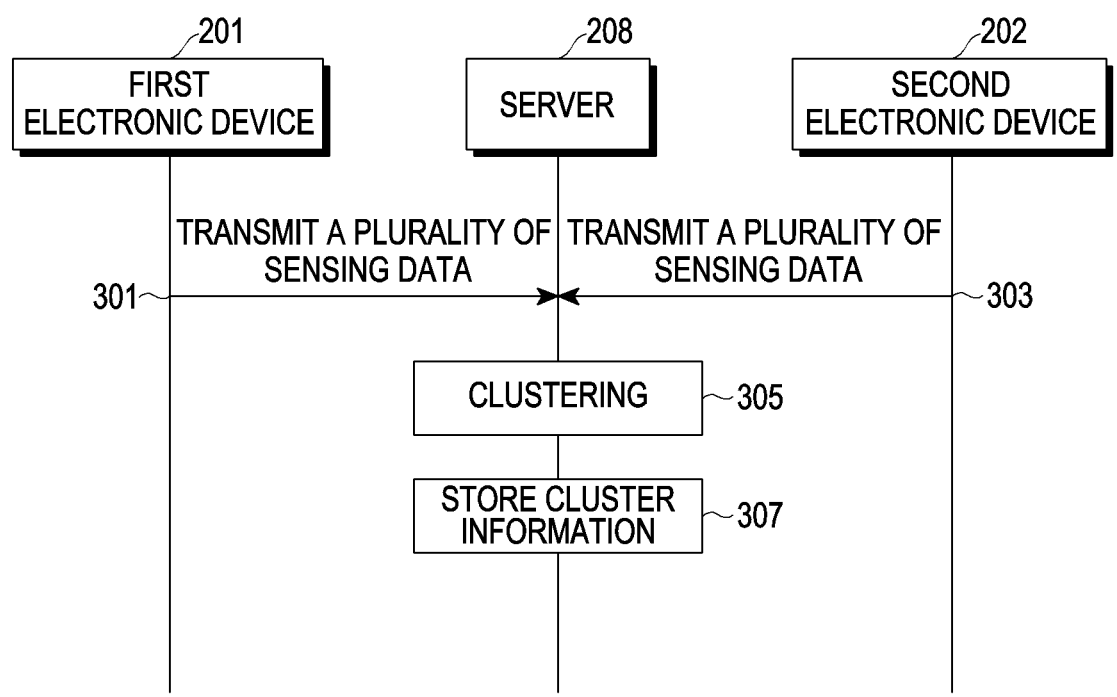

FIGS. 3A, 3B and 3C are diagrams illustrating an operation of clustering a plurality of data by a server according to certain embodiments.

Referring to FIG. 3A, when obtaining sensing data, the first electronic device 201 may transmit the plurality of sensing data to the server 208 in operation 301. In operation 302, when obtaining sensing data, the second electronic device 202 may also transmit the sensing data to the server 208. Each of the first electronic device 201 and the second electronic device 202 may obtain sensing data corresponding to user activities and transmit the obtained sensing data to the server 208, in response to the user activities. That is, the server 208 may obtain sensing data from each of the first electronic device 201 and the second electronic device 202. Further, the server 208 may store the sensing data received from each of the first electronic device 201 and the second electronic device 202 in the database 235.

The server 208 may cluster the obtained plurality of sensing data in operation 305.

The server 208 may generate data packets (or activity data packets) using the sensing data before the clustering. Further, the server 208 may generate the data packets by additionally using user information. For example, the server 208 may generate the data packets as illustrated in FIG. 3B. The data packet illustrated in FIG. 3B is merely an example, which should not be construed as limiting the technical spirit of the present disclosure.

According to certain embodiments, the first electronic device 201 may generate a data packet. The first electronic device 201 may store the data packet in the memory 230. Further, the first electronic device 201 may transmit the data packet to the server 208.

According to certain embodiments, the server 208 may select at least a part of data included in the data packet as a variable. For example, the server 208 may deem data that is likely to be collected as a result of user activity, as a variable. For example, the server 208 may consider as variables, data about "distance", "number of steps", "speed", "calories", and "heart rate" as illustrated in FIG. 3C. The data types illustrated in FIG. 3C are merely examples, which should not be construed as limiting the technical spirit of the present disclosure.

The server 208 may normalize the data corresponding to the selected variables and extract principal components of the normalized data. Further, the server 208 may select at least one of the extracted principal components and cluster data corresponding to selected variables based on the selected at least one principal component. A clustering method will be described in detail with reference to FIGS. 4A and 4B.

In operation 307, the server 208 performs clustering and store cluster information in the database 235. It should be understood that in certain embodiments, the functions performed by the server can be performed by the first electronic device 201.

Figure 4A:
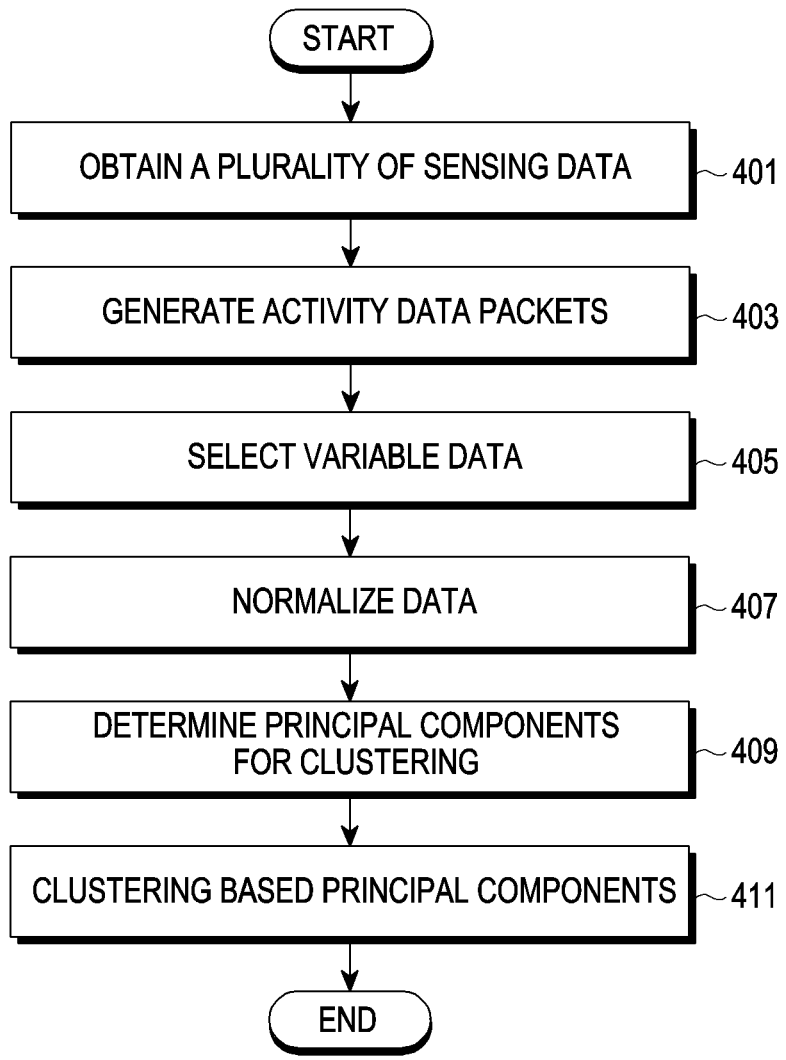
FIGS. 4A and 4B are diagrams illustrating an operation of performing clustering by a server or an electronic device according to certain embodiments.
Figure 4B:
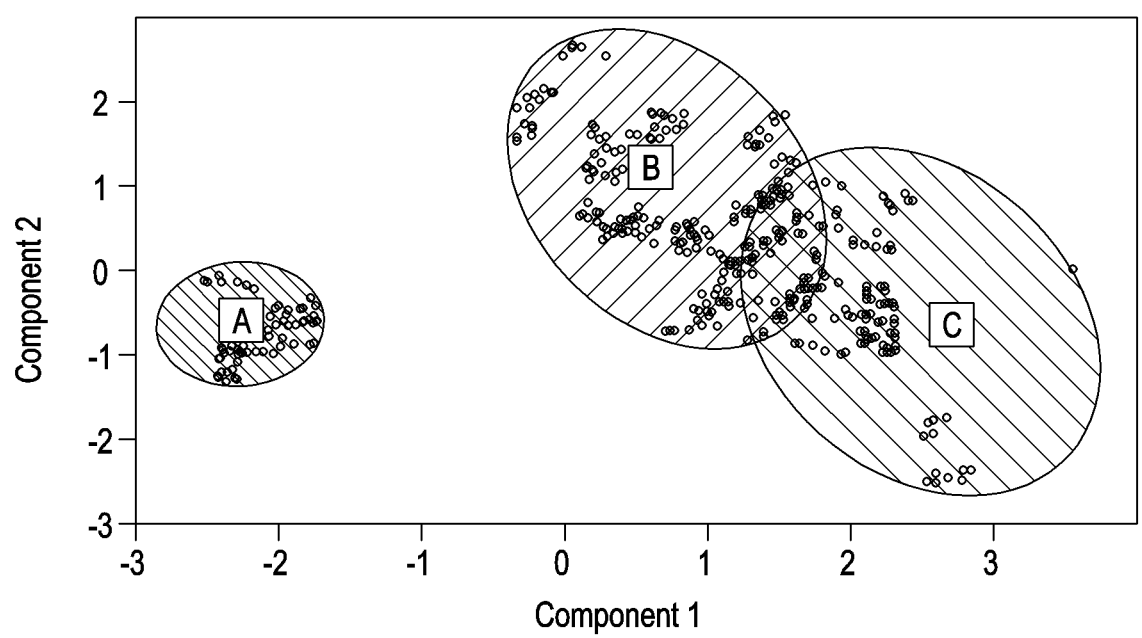

FIGS. 4A and 4B are diagrams illustrating a clustering operation of a server or an electronic device according to certain embodiments, though the operations can be performed on a first electronic device 201 in certain embodiments.

Referring to FIG. 4A, a server (for example, the server 208 of FIG. 2) may obtain a plurality of sensing data from external electronic devices (for example, the first electronic device 201 and the second electronic device 202) in operation 401. For example, the server 208 may obtain a plurality of sensing data periodically or aperiodically from the external electronic devices 201 and 202.

In operation 403, the server 208 may generate data packets (or activity data packets) by using the plurality of sensing data.

In operation 405, the server 208 may select, as variables, at least a part of data included in the data packets. For example, the server 208 may select data which is highly probable to be sensed in a user activity, as variables. This is because sensing data about a user activity may be missed according to the types of sensors included in the external electronic devices and thus missed values may exist irregularly.

In operation 407, the server 208 may normalize data corresponding to the selected variables.

In operation 409, the server 208 may determine principal components of the normalized data. For example, the server 208 may extract the principal components from the normalized data by a specific algorithm (for example, principal component analysis (PCA) algorithm) for extracting principal components. Further, the server 208 may select at least one of the extracted principal components. For example, the server 208 may select principal components occupying 70% of the whole in the distribution of the principal components. In certain embodiments, the principal components fall between the $15^{th}$ percentile and the $85^{th}$ percentile can be selected, or within approximately one-half standard deviation from the median in a Gaussian distribution. For example, when the server 208 extracts five principal components and two high-ranking components occupy 70% of the whole, the server 208 may determine the high-ranking two components as principal components. For example, the number of the determined principal components may determine the dimensions of clusters. For example, when two principal components are determined, the server 208 may obtain two-dimensional (2D) clusters. When three principal components are determined, the server 208 may obtain three-dimensional (3D) clusters.

In operation 411, the server 208 may cluster the data corresponding to the variables selected based on the selected principal components. For example, the server 208 may perform the clustering by a specific cluster algorithm (for example, K-means algorithm). The number of clusters may be optimized by the specific clustering algorithm. The server 208 may obtain a plurality of clusters as a result of the clustering. For example, the server 208 may obtain three 2D clusters based on two principal components as illustrated in FIG. 4B. For example, the server 208 may obtain cluster A, cluster B, and cluster C for the data corresponding to selected variables, as illustrated in FIG. 4B. In certain embodiments, the vertical axis can be heartbeats per second, while the horizontal axis time into a particular activity. In certain embodiments, the vertical access can be the heart rate, while the horizontal access can be a reading of the accelerometer. Cluster A can, for example, correspond to walking, while cluster B can correspond to jogging. Cluster C can correspond to riding a bicycle.

According to certain embodiments, the server 208 may determine a cluster corresponding to sensing data from among the plurality of clusters. The server 208 may determine a similarity value based on the relationship between the sensing data and the determined cluster and the features of the determined cluster. The operation of determining a similarity value will be described later with reference to FIG. 5.

While the server 208 has been described as performing clustering in FIGS. 4A and 4B, the first electronic device 201 may also perform clustering in the above-described method.

Figure 5:
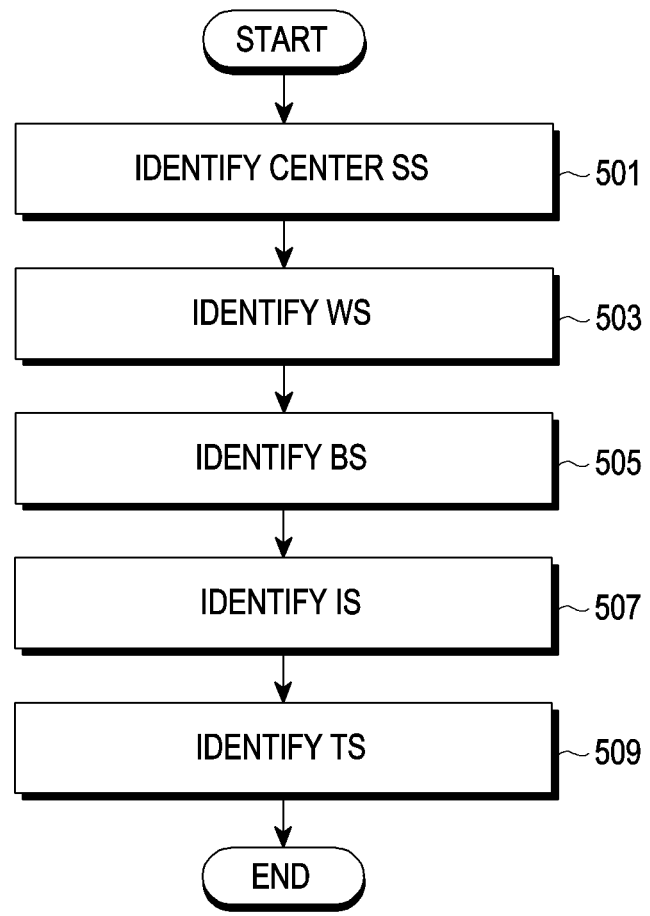
FIG. 5 is a flowchart illustrating an operation of identifying a similarity between newly obtained data and a cluster corresponding to the data by a server or an electronic device according to certain embodiments.

FIG. 5 is a flowchart illustrating an operation of identifying a similarity value between newly obtained sensing data and a cluster corresponding to the sensing data by a server or an electronic device according to certain embodiments.

Referring to FIG. 5, the server 208 may determine a first cluster corresponding to newly obtained first sensing data from among a plurality of clusters and determine (or identify) how similar the first sensing data is to common features of existing user activity-related data. For example, the similarity value of the first sensing data may indicate the degree to which the first sensing data is similar to the common features of the existing user activity-related data. For example, the first cluster may be a cluster closest to the first sensing data or a cluster including the first sensing data.

According to certain embodiments, the server 208 may identify a center similarity score (SS) indicating how similar the first sensing data is to the center of the first cluster in operation 501. For example, the server 208 may identify the center SS by measuring the angle between the vector of the first sensing data and the vector of the center of the first cluster. For example, the server 208 may identify the center SS by the following Equation 1. In Equation 1, A may be the vector of the center of the first cluster, and B (or Bi) may be a vector corresponding to the first sensing data. For example, n may be a natural number equal to or greater than 1. For example, the center SS may be a value greater than 0 and equal to or less than 1. As the center SS is closer to 1, this may imply that the first sensing data is more similar to the center of the first cluster.

$$sim(A, B) = \cos(\theta) = \frac{A \cdot B}{\|A\| \cdot \|B\|} = \frac{\sum_{i=1}^{n} A \times B_i}{\sqrt{(A)^2} \times \sqrt{\sum_{i=1}^{n} (B_i)^2}}$$ [Equation 1]

In operation 503, the server 208 may identify a witness score (WS) indicating how much data included in the first cluster are concentrated around the center of the first cluster or how much distinctive the unique features of the data included in the first cluster are. For example, the WS may be the sum of the distances between the coordinates of the data included in the first cluster and the average coordinates of the data included in the first cluster. For example, the server 208 may identify the WS by Equation 2. For example, as the WS is closer to 0, this may indicate a higher concentration or feature uniqueness, whereas a higher value may indicate more sparse data. In certain embodiments, the Withness Score can be the variance or a score that is a function of the variance of the data.

$$W(C_k) = \Sigma_{\in C_k}(x_i - \mu_k)^2$$ [Equation 2]

where:
$x_i$ is a data point belonging to the cluster $C_k$
$\mu_k$ is the mean value of the points assigned to the cluster $C_k$ In certain embodiments, the formula can be divided by the number of points.

In operation 505, the server 208 may identify a betweenness score (BS) indicating how independently the sensing data has been generated. For example, the BS may be the sum of the distances between the data of the first cluster and the coordinates of the centers of other clusters. For example, the server 208 may identify the BS by Equation 3. For example, as the BS is closer to 0, this may mean that more similar components are shared between the clusters.

$$B(C_k) = \Sigma_{\in C_k}(x_i - \mu_k)^2$$ [Equation 3]

where:
$x_i$ is a data point of target k cluster centroid
$\mu_k$ is a data point of $C_k$ centroid except target cluster In certain embodiments, the betweenness score can be a score that is a function of a measure of the distance between data clusters.

In operation 507, the server 208 may identify an intersection score (IS) indicating how much the first cluster overlaps with a neighbor cluster. For example, the IS may be the overlap ratio of the first cluster to another cluster. The IS may be the average of the product of a distance between overlap points of the first cluster and at least one overlapped cluster and a distance between points orthogonal to the overlap points. For example, the server 208 may identify the IS by Equation 4. For example, n may be a natural number equal to or greater than 1 in Equation 4. Further, a function d may be a function of calculating the distance between two points in Equation 4. For example, as the IS is closer to 0, this may indicate a less similarity.

$$\frac{\sum_{xi,xj,xq,xr \in Ck}^{n} d(xj - xi)d(xr - xq)}{n}$$ [Equation 4]

where:

xi xj are the data point of overlapped cluster k except already checked xq xr are the data point of orthogonal overlapped cluster k except already checked In operation 509, the server 208 may identify a total score (TS) (or a similarity value) by using the SS, the WS, the BS, and the IS. For example, the server 208 may identify the TS by Equation 5. For example, as the TS is smaller, this may indicate a greater similarity.

$$TS = \sqrt{\frac{WS + BS}{SS + IS}}$$ [Equation 5]

The order of identifying the center SS, the WS, the BS, and the IS may be different from that illustrated in FIG. 5. That is, the order of identifying the center SS, the WS, the BS, and the IS in FIG. 5 is provided for the convenience of description, not limited to FIG. 5.

Figures 6A, 6B:
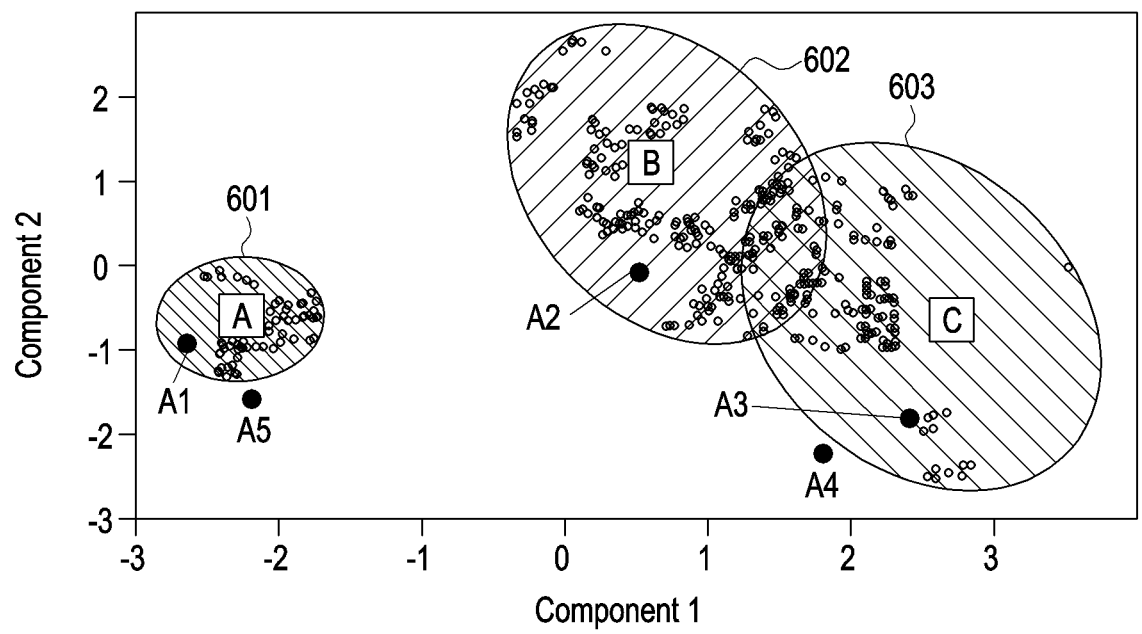
FIGS. 6A and 6B are diagrams illustrating an operation of identifying a similarity between newly obtained data and a cluster corresponding to the data by a server or an electronic device according to certain embodiments.

FIGS. 6A and 6B are diagrams illustrating an operation of identifying a similarity between newly obtained data and a cluster corresponding to the data by a server or an electronic device according to certain embodiments.

Referring to FIG. 6A, according to certain embodiments, the server 208 may cluster data related to user activities and obtain a plurality of clusters 601, 602 and 603.

According to certain embodiments, the server 208 may obtain five new sensing data, data points. The server 208 may identify similarities between the existing clusters and the new sensing data. Alternatively, the server 208 may obtain new clusters by adding the new sensing data to the existing clusters and identify similarities between the obtained clusters and the new sensing data. For example, the server 208 may identify the similarities by comparing three clusters with the five new sensing data. For example, the new sensing data may be A1, A2, A3, A4, and A5. For example, the data A1 may be located within a cluster A 601, and its closest cluster may also be the cluster A 601. The data A2 may be located within a cluster B 602, and its closest cluster may also be the cluster B 602. The data A3 located within a cluster C 603, and its closest cluster may also be the cluster C 603. The data A4 may be located outside the cluster C 603 and its closest cluster may be the cluster C 603. The data A5 may be located outside the cluster A 601, and its closest cluster may also be the cluster A 601.

Referring to FIG. 6B, according to certain embodiments, the server 208 may identify the similarities of the new sensing data points A1, A2, A3, A4, and A5. For example, the server 208 may identify the similarities of the new sensing data or data points (now referred to as data) A1, A2, A3, A4, and A5 by measuring the center CS, WS, BS, and IS of each of the new sensing data A1, A2, A3, A4, and A5. For example, the similarity (i.e., TS) SS may be '3.18' for the data A1, '1.35' for the data A2, '1.36' for the data A3, '1.39' for the data A4, and '4.95' for the data A5. It may be noted from the similarities that the data A2, A3, and A4 are located in areas concentrated with principal components, have small similarities, and thus are similar to existing data related to user activities. In contrast, it may be noted that the data A1 and the data A5 have high similarities due to a small number of components shared by the neighbor cluster A 601 and are not similar to existing data related to user activities.

According to certain embodiments, a first electronic device (for example, the first electronic device 201 of FIG. 2) may determine that the data A2, the data A3, and the data A4 having low similarities are highly reliable. Further, the first electronic device 201 may determine that the data A1 and the data A5 having high similarities and have low reliability. A reliability value may be determined based on a similarity.

While the server 208 has been described as an entity responsible for identifying a similarity in FIGS. 5, 6A and 6B for the convenience of description, the first electronic device 201 may also identify a similarity in the above-described method. For example, the first electronic device 201 may perform at least a part of the above-described operations of identifying a similarity.

Figure 7A:
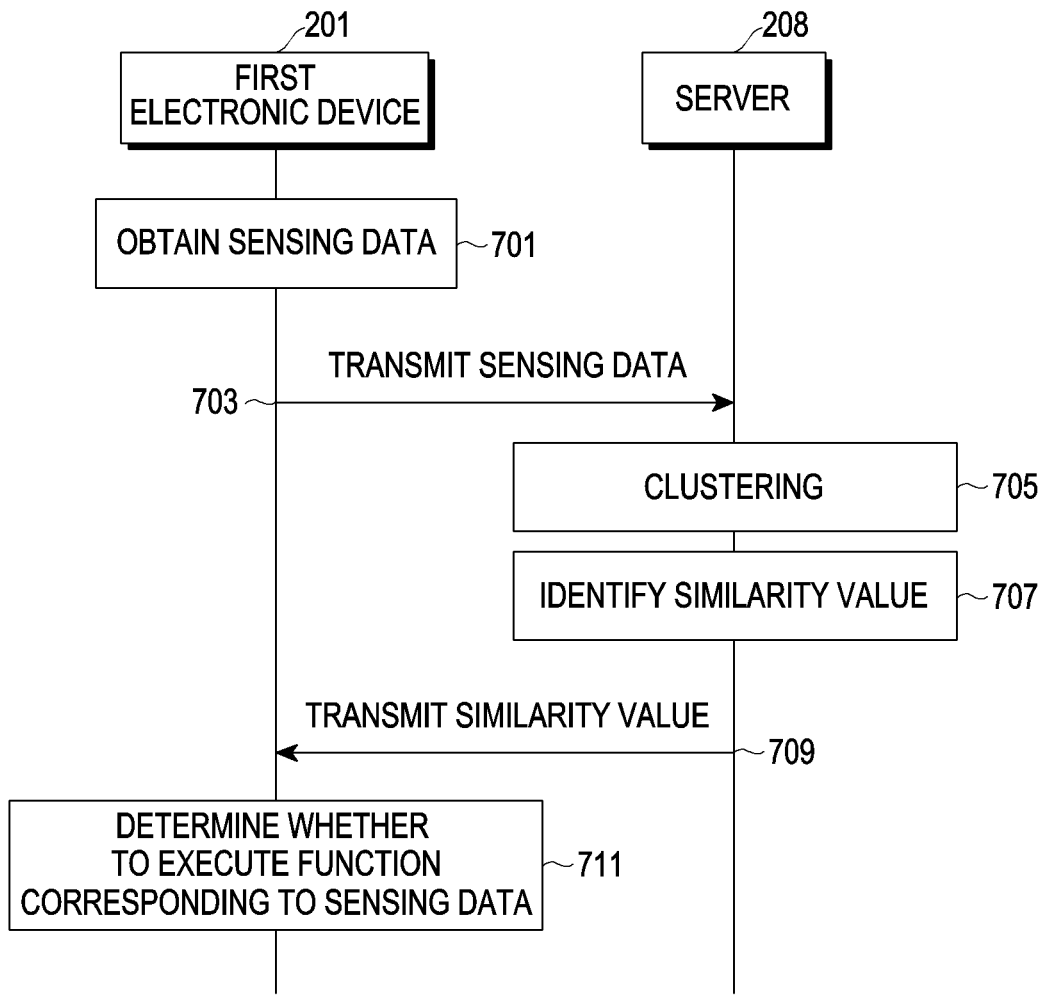
FIGS. 7A, 7B and 7C are diagrams illustrating an operation of executing a function corresponding to newly obtained data based on a result of a comparison between the newly obtained data and cluster information by an electronic device according to certain embodiments.
Figure 7B:
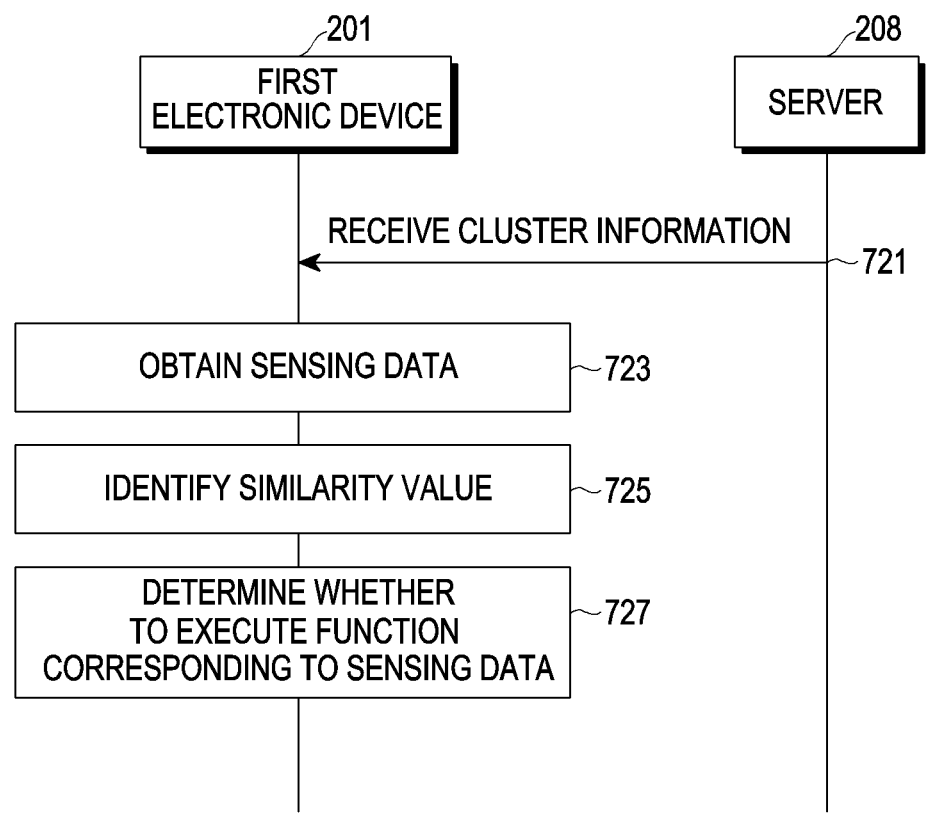
Figure 7C:
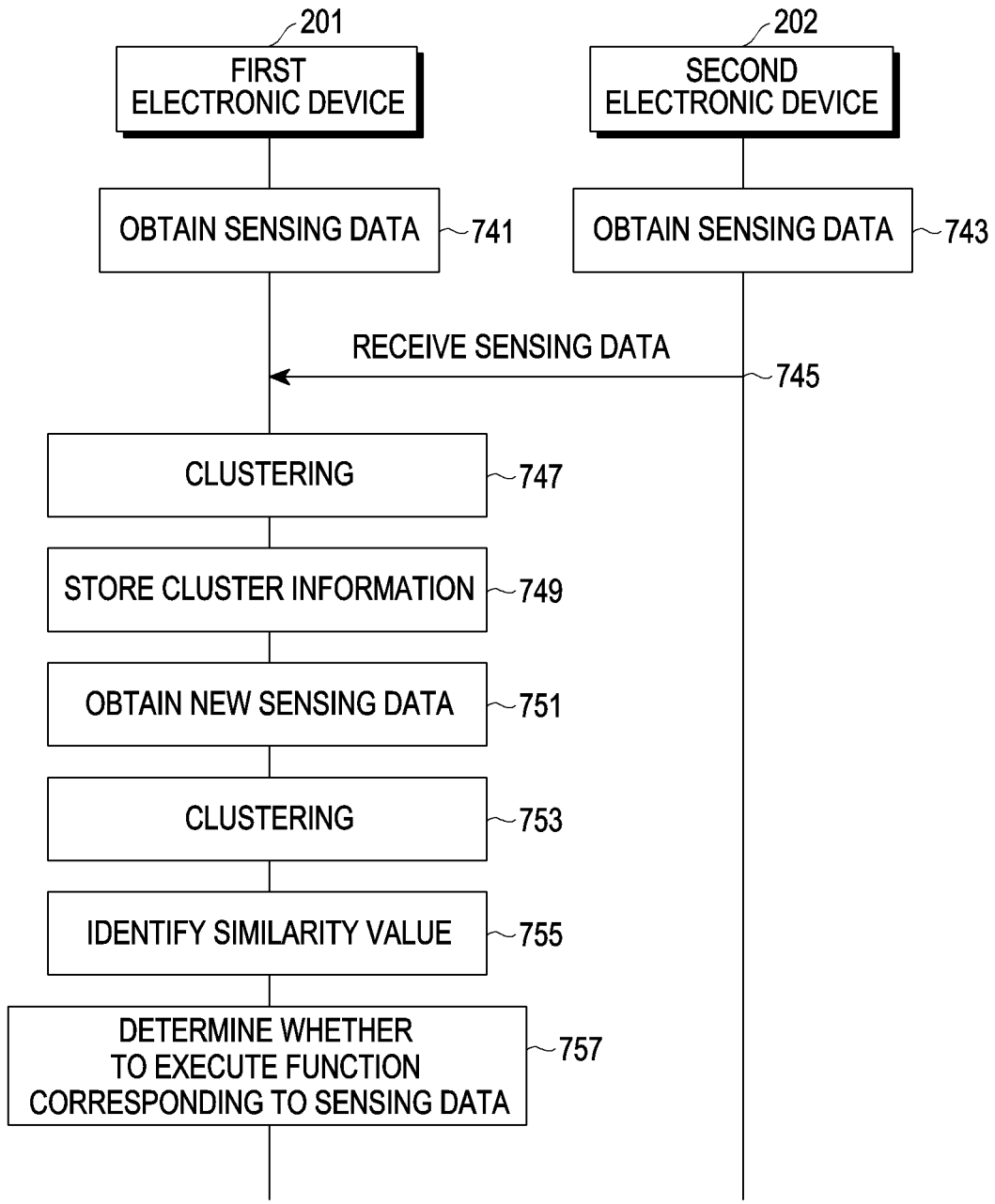

FIGS. 7A, 7B and 7C are diagrams illustrating an operation of executing a function corresponding to newly obtained data based on the result of a comparison between the newly obtained data and cluster information according to certain embodiments.

FIG. 7A is a diagram illustrating an operation of identifying a similarity through the server 208 and performing an operation corresponding to sensing data by an electronic device (for example, the first electronic device 201 of FIG. 2).

Referring to FIGS. 7A, 7B and 7C, an operation of performing clustering and an operation of identifying a similarity may be based on the description of FIGS. 4A to 6.

Referring to FIG. 7A, according to certain embodiments, the first electronic device 201 may obtain sensing data through a plurality of sensors in response to a user activity in operation 701. In operation 703, the first electronic device 201 may transmit the sensing data to the server 208.

According to certain embodiments, the server 208 may cluster data related to user activities by additionally reflecting the newly obtained sensing data in cluster information pre-stored in the database 235 in operation 705. The server 208 may obtain a plurality of clusters by the clustering. In operation 707, the server 208 may identify the similarity of the sensing data by using the plurality of clusters.

According to certain embodiments, the server 208 may identify the similarity of the sensing data without clustering. For example, the server 208 may identify the similarity of the sensing data by obtaining a plurality of clusters from the cluster information pre-stored in the database 235.

According to certain embodiments, the server 208 may transmit the similarity to the first electronic device 201 in operation 709.

According to certain embodiments, the first electronic device 201 may determine whether to execute a function corresponding to the sensing data based on the similarity in operation 711. For example, the first electronic device 201 may or may not execute the function corresponding to the sensing data based on the similarity of the sensing data.

FIG. 7B is a diagram illustrating an operation of identifying a similarity and executing a function corresponding to sensing data according to the similarity by an electronic device (for example, the first electronic device 201 of FIG. 2) according to certain embodiments.

Referring to FIG. 7B, according to certain embodiments, the first electronic device 201 may receive cluster information from the server 208 in operation 721. For example, the cluster information may be cluster information that the server 208 has obtained by clustering data related to user activities and stored in the database 235. For example, the cluster information may include information about a plurality of clusters related to the user activities.

According to certain embodiments, the first electronic device 201 may obtain sensing data through a plurality of sensors in response to a user activity in operation 723. In operation 725, the first electronic device 201 may identify the similarity of the sensing data by using the plurality of clusters included in the cluster information.

According to certain embodiments, the first electronic device 201 may determine whether to execute a function corresponding to the sensing data based on the similarity in operation 727. For example, the first electronic device 201 may or may not execute the function corresponding to the sensing data based on the similarity of the sensing data.

According to certain embodiments, the first electronic device 201 may receive the cluster information after obtaining the sensing data. For example, after obtaining the sensing data, the first electronic device 201 may request cluster information to the server 208. The server 208 may transmit the cluster information to the first electronic device 201 in response to the request of the first electronic device 201.

FIG. 7C is a diagram illustrating an operation of executing a function corresponding to sensing data by identifying a similarity without intervention of a server by an electronic device (for example, the first electronic device 201 of FIG. 2).

Referring to FIG. 7C, according to certain embodiments, the first electronic device 201 may obtain sensing data through a plurality of sensors in operation 741. Further, the second electronic device 202 may obtain sensing data through sensors in operation 743. In operation 745, the first electronic device 201 may receive the sensing data from the second electronic device 202.

According to certain embodiments, the first electronic device 201 may obtain a plurality of sensing data and cluster the plurality of sensing data in operation 747. In operation 749, the first electronic device 201 may store cluster information obtained by the clustering in the memory 230.

According to certain embodiments, the first electronic device 201 may obtain new sensing data through a plurality of sensors in response to a user activity in operation 751.

According to certain embodiments, the first electronic device 201 may add the newly obtained sensing data to the cluster information stored in the memory 230 and perform clustering on the resulting data in operation 753. The first electronic device 201 may obtain a plurality of clusters by the clustering. In operation 755, the first electronic device 201 may identify the similarity of the sensing data by using the plurality of clusters.

According to certain embodiments, the first electronic device 201 may identify the similarity of the sensing data without additional clustering. For example, the first electronic device 201 may identify the similarity of the new sensing data by obtaining a plurality of clusters from the cluster information stored in the memory 230.

According to certain embodiments, the first electronic device 201 may determine whether to execute a function corresponding to the sensing data based on the similarity in operation 757. For example, the first electronic device 201 may or may not execute the function corresponding to the sensing data based on the similarity of the sensing data.

Figure 8:
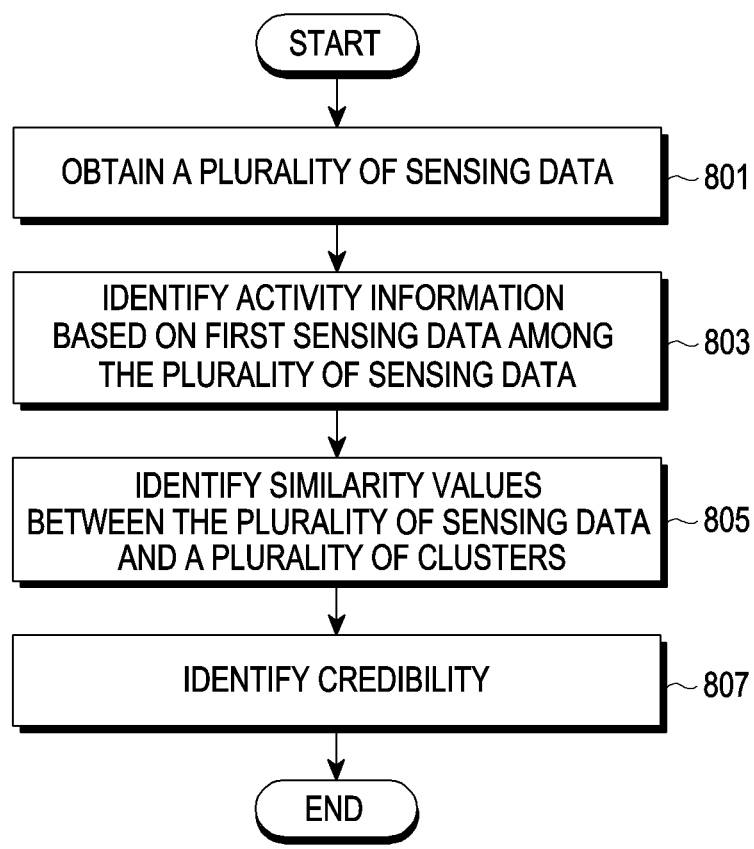
FIG. 8 is a flowchart illustrating an operation of identifying the reliability of sensing data by identifying similarities between a plurality of clusters and sensing data including first sensing data based on which activity information is identified and other sensing data by an electronic device according to certain embodiments.

FIG. 8 is a flowchart illustrating an operation of identifying the reliability of sensing data by identifying similarities between a plurality of clusters and sensing data including first sensing data and other sensing data, the first sensing data being used to identify activity information by an electronic device according to certain embodiments.

Referring to FIG. 8, according to certain embodiments, a first electronic device (for example, the first electronic device 201 of FIG. 2) may obtain sensing data in operation 801. For example, the first electronic device 201 may obtain sensing data through the sensor module 270 in response to a user activity, and obtain sensing data from another electronic device (for example, the second electronic device 202). For example, the sensing data may include first sensing data used to identify specific user activity information. Further, the plurality of sensing data may include second sensing data which is not used to identify the specific user activity information. For example, the first sensing data may include sensing data of an accelerometer sensor and/or sensing data of a gravity sensor. The second sensing data may include heart rate data and/or GPS data.

According to certain embodiments, the first electronic device 201 may identify the specific activity information based on the first sensing data among the plurality of sensing data in operation 803. For example, the specific user activity information may include information about the number of steps that the user has taken.

According to certain embodiments, the first electronic device 201 may identify similarities between the plurality of sensing data and a plurality of clusters in operation 805. For example, the first electronic device 201 may identify a similarity between each of the plurality of sensing data and each of the plurality of clusters. That is, the first electronic device 201 may identify similarities between the first sensing data and each of the plurality of clusters. Further, the first electronic device 201 may also identify similarities between the sensing data other than the first sensing data and each of the plurality of clusters.

In operation 807, the first electronic device 201 may identify the reliability of the first sensing data based on the similarity of each of the plurality of sensing data. For example, the first electronic device 201 may identify whether the heart rate data as well as the acceleration data is similar to the common features of existing data related to the user activities in order to identify the reliability of the specific activity information (e.g., the information about the number of steps) about the user. Therefore, the first electronic device 201 may identify the reliability of the acceleration data. That is, when the first electronic device 201 identifies that the heart rate data as well as the acceleration data is similar to the common features of the existing data related to the user activities, the first electronic device 201 may determine that the information about the number of steps based on the acceleration data is highly credible.

Figure 9A:
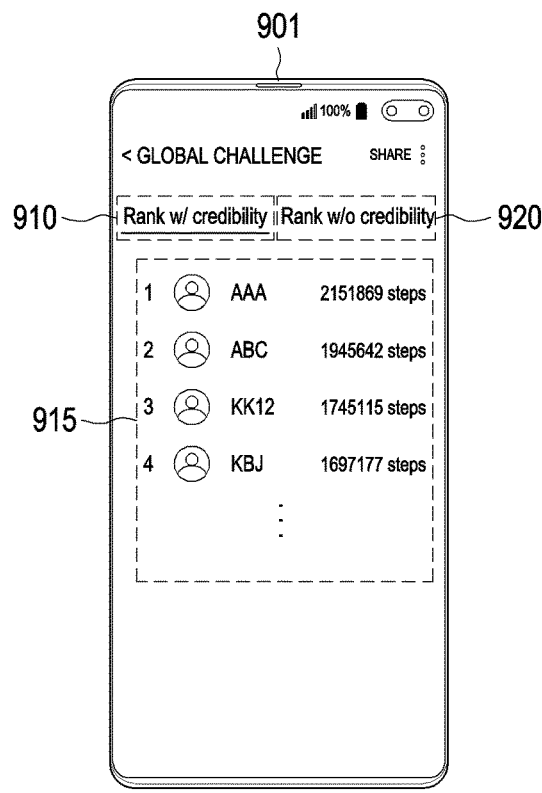
FIGS. 9A and 9B are diagrams illustrating user interfaces referred to for describing an operation of identifying the reliability of sensing data by an electronic device according to certain embodiments.
Figure 9B:
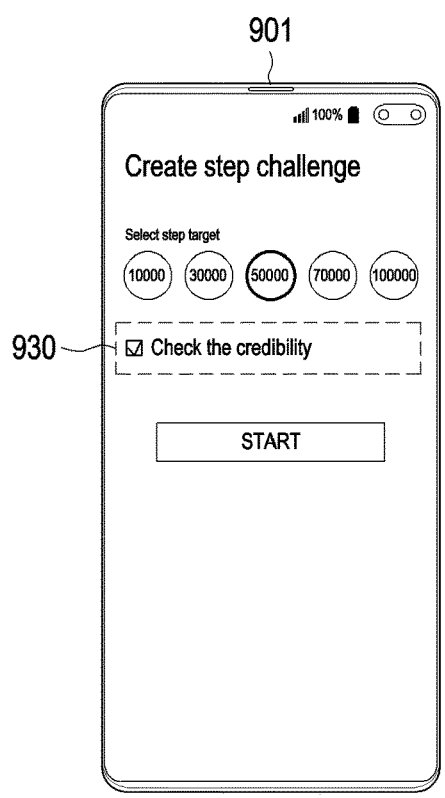

FIGS. 9A and 9B illustrate user interfaces referred to for describing an operation of identifying the reliability of sensing data by an electronic device according to certain embodiments.

Referring to FIGS. 9A and 9B, an electronic device 901 (for example, the first electronic device 201 of FIG. 2) may provide data filtered according to a reliability.

Referring to FIG. 9A, according to certain embodiments, upon user selection of an object 910 requesting the ranks of data filtered according to credibilities, the electronic device 901 may provide the ranks of the filtered data according to the credibilities on a display window 915. For example, the electronic device 901 may rank only numbers of steps corresponding to sensing data with credibilities equal to or greater than a preset value and provide the ranked numbers of steps on the display window.

According to certain embodiments, upon user selection of an object 920 requesting the ranks of all data irrespective of their credibilities, the electronic device 901 may provide the ranks of all data on the display window 915 without considering the credibilities. For example, the electronic device 901 may rank numbers of steps that users have taken on the display window 915 without considering the credibilities of sensing data corresponding to the numbers of steps.

Referring to FIG. 9B, according to certain embodiments, upon user selection of an object 930 requesting filtered data according to credibilities, the electronic device 901 may use and/or store only the filtered data according to the credibilities. For example, upon use selection of the object 930, only when the reliability of sensing data is equal to or greater than a predetermined value, the electronic device 901 may count the number of steps corresponding to the sensing data. Further, when the reliability of sensing data is less than the predetermined value, the electronic device 901 may discard the sensing data without using and/or storing the sensing data.

Figure 10:
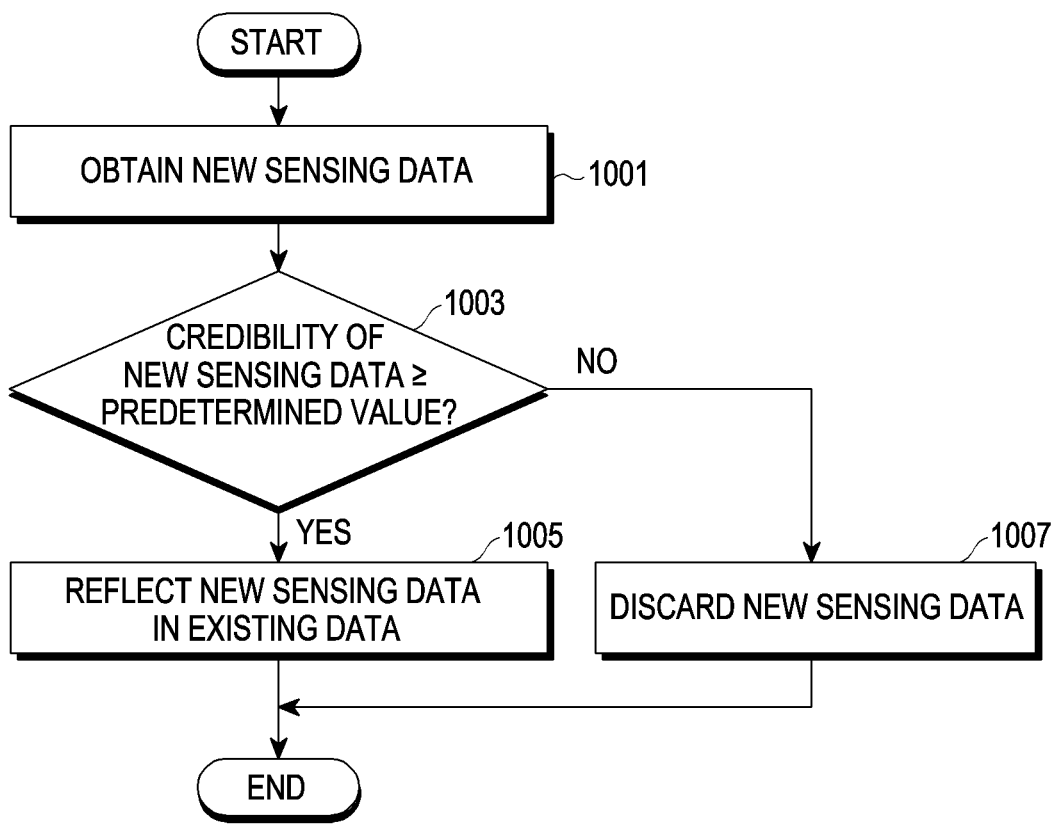
FIG. 10 is a flowchart illustrating an operation of executing a function according to the reliability of new data by an electronic device according to certain embodiments.

FIG. 10 is a flowchart illustrating an operation of executing a function according to the reliability of new data by an electronic device according to certain embodiments.

Referring to FIG. 10, a first electronic device (for example, the first electronic device 201 of FIG. 2) may obtain new sensing data. For example, the first electronic device 201 may obtain the new sensing data in response to a user activity.

According to certain embodiments, in operation 1003, the first electronic device 201 may identify whether the reliability of the new sensing data is equal to or greater than a predetermined value. For example, the first electronic device 201 may identify a similarity value of the new sensing data using cluster information, and identify the reliability of the sensing data based on the similarity value.

According to certain embodiments, when the reliability of the new sensing data is equal to or greater than the predetermined value (yes in operation 1003), the first electronic device 201 may reflect the new sensing data in existing data in operation 1005.

According to certain embodiments, when the reliability of the new sensing data is less than the predetermined value (no in operation 1003), the first electronic device 201 may discard the new sensing data in operation 1007.

Figure 11A:
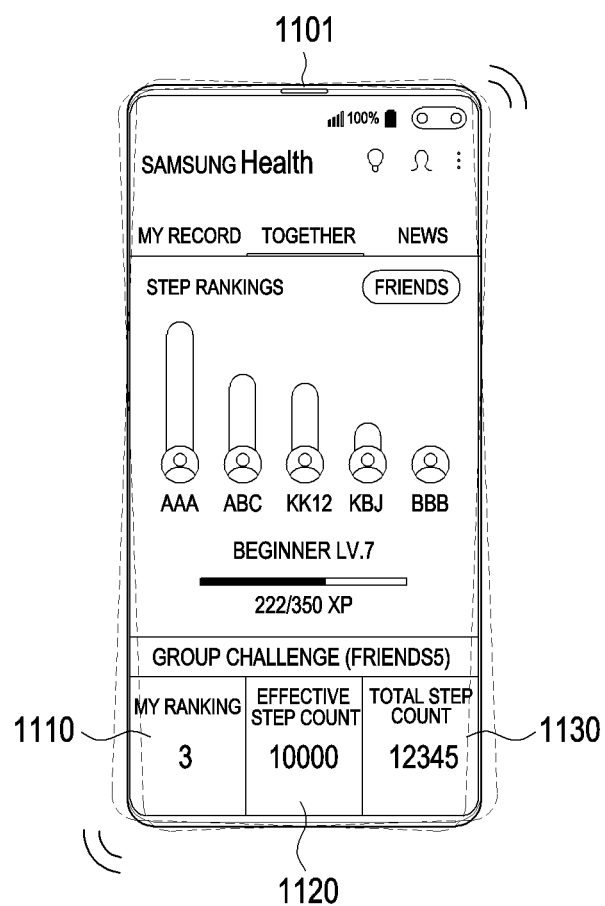
FIGS. 11A and 11B are diagrams illustrating user interfaces referred to for describing an operation of executing a function according to the reliability of new data by an electronic device according to certain embodiments.
Figure 11B:
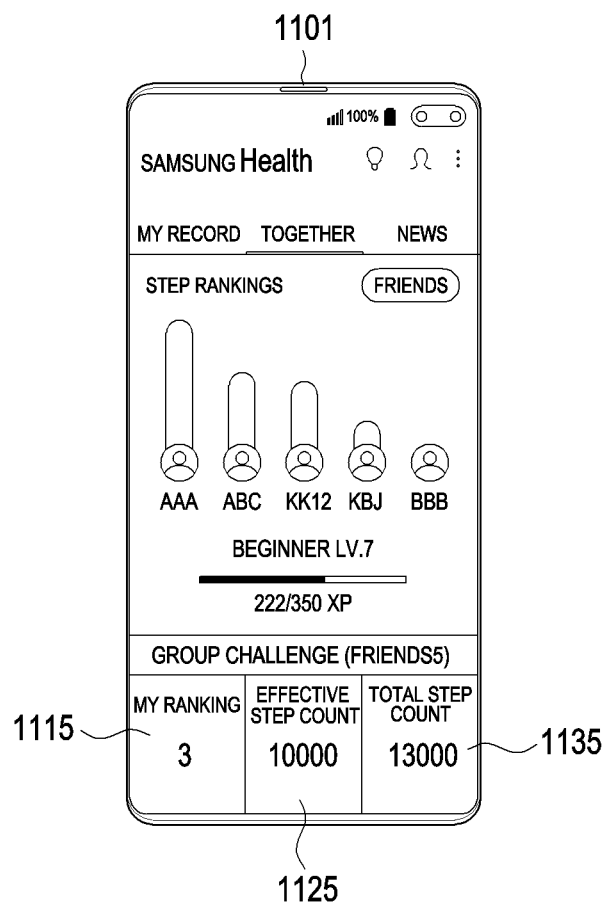

FIGS. 11A and 11B are user interfaces referred to for describing an operation of executing a function according to the reliability of new data by an electronic device according to certain embodiments.

FIGS. 11A and 11B, an electronic device 1101 (for example, the first electronic device 201 of FIG. 2) may obtain sensing data through a sensor module (for example, the sensor module 270 of FIG. 2) in response to a user activity and count the number of steps of a user.

Referring to FIG. 11A, according to certain embodiments, the electronic device 1101 may provide information about the number of steps by counting the number of steps of the user. For example, the electronic device 1101 may provide information 1120 about the number of effective steps and/or information 1130 about the total number of steps. Additionally, the electronic device 1101 may provide a ranking 1110 for the number of effective steps among users included in a specific group.

According to certain embodiments, the electronic device 1101 may identify a similarity value of the sensing data related to the number of steps of the user in response to a movement of the electronic device 1101 (for example, the sensing data can be a data point of the number of counted steps and the distance moved). For example, the electronic device 1101 may autonomously identify the similarity value or may identify the similarity value through a server (for example, the server 208 of FIG. 2). The electronic device 1101 may identify the reliability of the sensing data based on the similarity value of the sensing data. For example, the electronic device 1101 may obtain sensing data according to shaking of the electronic device 1101 that is different from an actual step of the user. The electronic device 1101 may identify that the sensing data is different from the existing sensing data about the user's steps.

Referring to FIG. 11B, according to certain embodiments, when the reliability of the sensing data is less than a predetermined value, the electronic device 1101 may not include the number of steps corresponding to the sensing data in the effective step count. For example, the electronic device 1101 may provide information 1135 about the total number of steps including the number of steps corresponding to the sensing data. For example, the total number of steps may be increased regardless of the reliability of the sensing data.

According to certain embodiments, the electronic device 1101 may provide information 1125 about the number of effective steps that do not include the number of steps corresponding to the sensing data. The electronic device 1101 may also provide a ranking 1115 for the number of effective steps that do not include the number of steps corresponding to the sensing data. For example, the number of effective steps may not be changed because the number of steps corresponding sensing data having a reliability less than the predetermined value is not included. In addition, the ranking based on the number of effective steps may not be changed in the group.

Figure 12A:
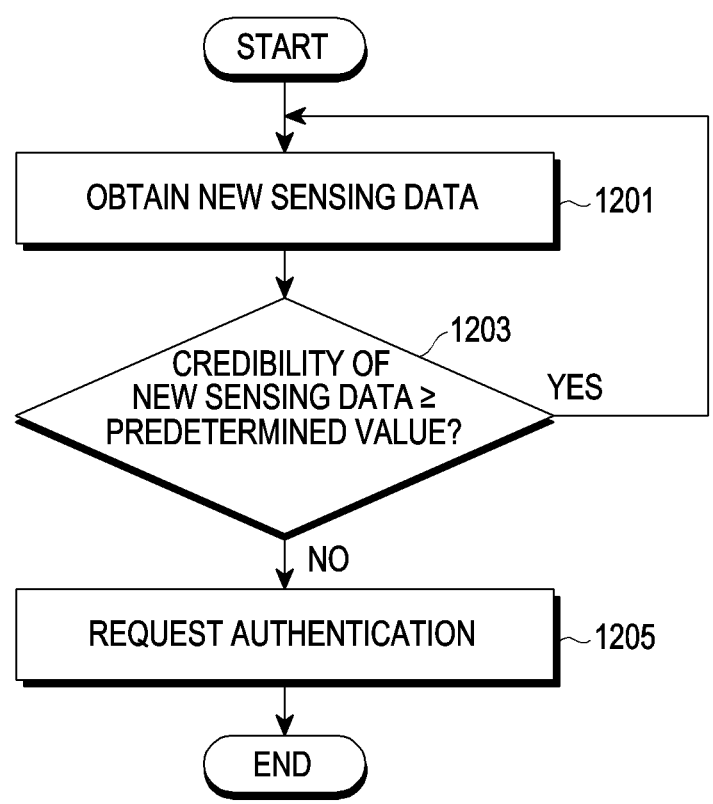
FIGS. 12A and 12B are diagrams illustrating an operation of executing a function according to the reliability of new data by an electronic device according to certain embodiments.
Figure 12B:
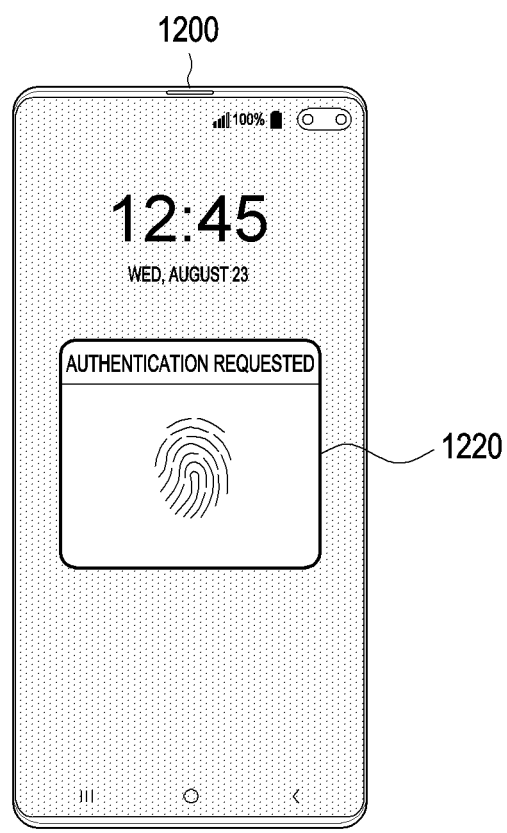

FIGS. 12A and 12B are diagrams referred to for describing an operation of executing a function according to the reliability of new data by an electronic device according to certain embodiments.

Referring to FIG. 12A, a first electronic device (for example, the first electronic device 201 of FIG. 2) may obtain new sensing data in operation 1201. For example, the first electronic device 201 may obtain new sensing data in response to a user activity.

According to certain embodiments, in operation 1203, the first electronic device 201 may identify whether the reliability of the new sensing data is equal to or greater than a predetermined value. For example, the first electronic device 201 may identify a similarity value of the new sensing data using cluster information and identify the reliability of the sensing data based on the similarity value.

According to certain embodiments, when the reliability of new sensing data is less than the predetermined value (no in operation 1203), the first electronic device 201 may request authentication to the user in operation 1205. For example, when the reliability of the new sensing data corresponding to the user activity is low, the first electronic device 201 may determine that the user activity is different from the existing user activity. Accordingly, the first electronic device 201 may request the user's authentication to identify whether the user matches the user of the first electronic device 201. For example, when the user's authentication is not completed, the first electronic device 201 may restrict execution of specified functions.

According to certain embodiments, if the reliability of the new sensing data is equal to or greater than the predetermined value (yes in operation 1203), the first electronic device 201 may not perform any further operation. Alternatively, the first electronic device 201 may monitor a user activity in real time or periodically through a plurality of sensors.

Referring to FIG. 12B, according to certain embodiments, an electronic device 1200 (for example, the first electronic device 201 of FIG. 2) display a window 1220 prompting authentication, when the reliability of newly obtained sensing data is less than a predetermined value. For example, the electronic device 1200 may perform authentication using a fingerprint, an iris, a face, a designated code, a designated motion, or a designated pattern. The electronic device 1200 may restrict execution of specified functions, when the user authentication is not completed.

Figure 13A:
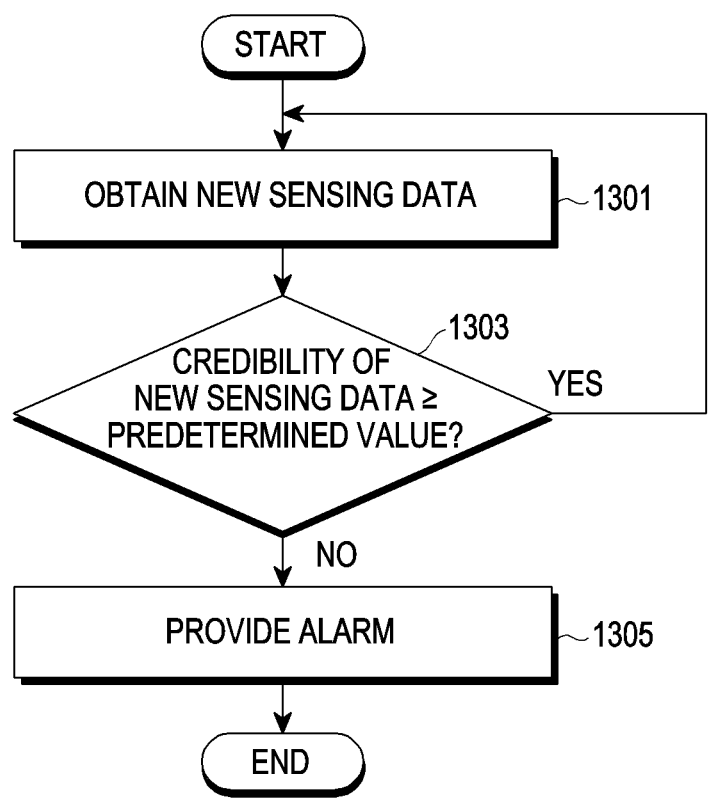
FIGS. 13A and 13B are diagrams illustrating an operation of executing a function according to the reliability of new data by an electronic device according to certain embodiments.
Figure 13B:
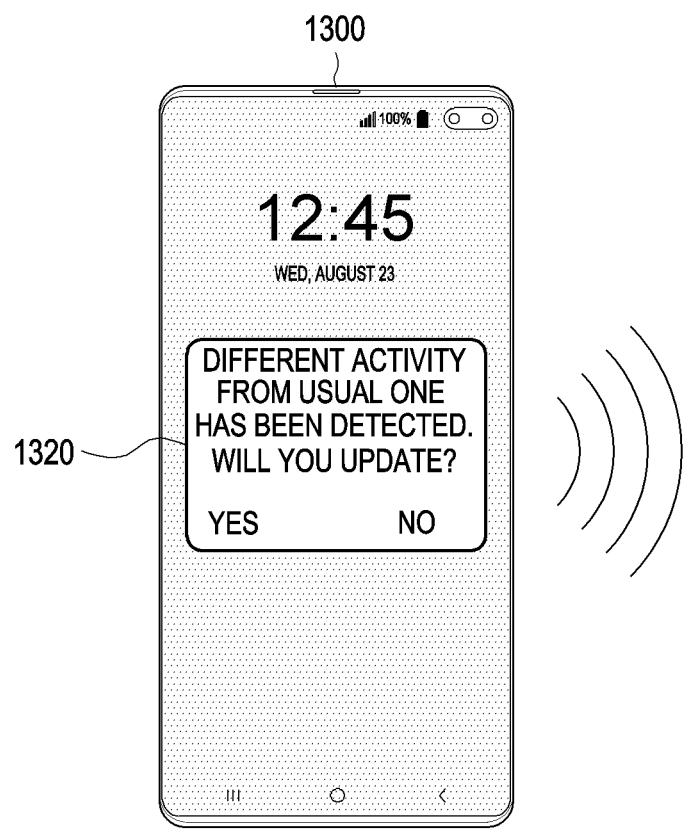

FIGS. 13A and 13B are diagrams referred to for describing an operation of executing a function according to the reliability of new data by an electronic device according to certain embodiments.

Referring to FIG. 13A, a first electronic device (for example, the first electronic device 201 of FIG. 2) may obtain new sensing data in operation 1301. For example, the first electronic device 201 may obtain new sensing data in response to a user activity.

According to certain embodiments, the first electronic device 201 may identify whether the reliability of the new sensing data is equal to or greater than a predetermined value in operation 1303. For example, the first electronic device 201 may identify a similarity value of the new sensing data using cluster information, and identify the reliability of the sensing data based on the similarity value.

According to certain embodiments, when the reliability of new sensing data is less than the predetermined value (no in operation 1303), the first electronic device 201 may provide an alarm in operation 1305. For example, the first electronic device 201 may provide the alarm by at least one of visual, auditory, or tactile means. For example, when the reliability of the new sensing data corresponding to the user activity is low, the first electronic device 201 may determine that the user activity is different from an existing user activity. Accordingly, the first electronic device 201 may determine that the user activity is not normal and thus provide an emergency alarm. Further, the first electronic device 201 may transmit an emergency call or an emergency message to a designated contact. For example, in the user's healthcare, the first electronic device 201 may analyze sensing data corresponding to a user activity to determine whether it is similar to an existing user activity. When determining that the user activity is not similar to the existing activity, the first electronic device 201 may provide an emergency alarm or transmit an emergency call or an emergency message.

According to certain embodiments, if the reliability of the new sensing data is equal to or greater than the predetermined value (yes in operation 1303), the first electronic device 201 may not perform any further operation. Alternatively, the first electronic device 201 may monitor a user activity in real time or periodically through a plurality of sensors.

Referring to FIG. 13B, according to certain embodiments, an electronic device 1300 (for example, the first electronic device 201 of FIG. 2) may display an alarm window 1320, when the reliability of newly obtained sensing data is less than a predetermined value. For example, the electronic device 1300 may notify that a user activity different from an existing one has been detected through the alarm window 1320. In addition, the electronic device 1300 may provide an alarm by a designated sound or vibration.

According to certain embodiments, the electronic device 1300 may determine whether to update the newly obtained sensing data to existing data according to a user's confirmation. For example, when receiving an input requesting an update from the user, the electronic device 1300 may update (or reflect) the newly obtained sensing data to the existing data. In this manner, the electronic device 1300 may obtain clustering information indicating a new characteristic of the user. Alternatively, when receiving an input that does not request an update from the user, the electronic device 1300 may discard the newly obtained sensing data without using or storing the data.

Figure 14:
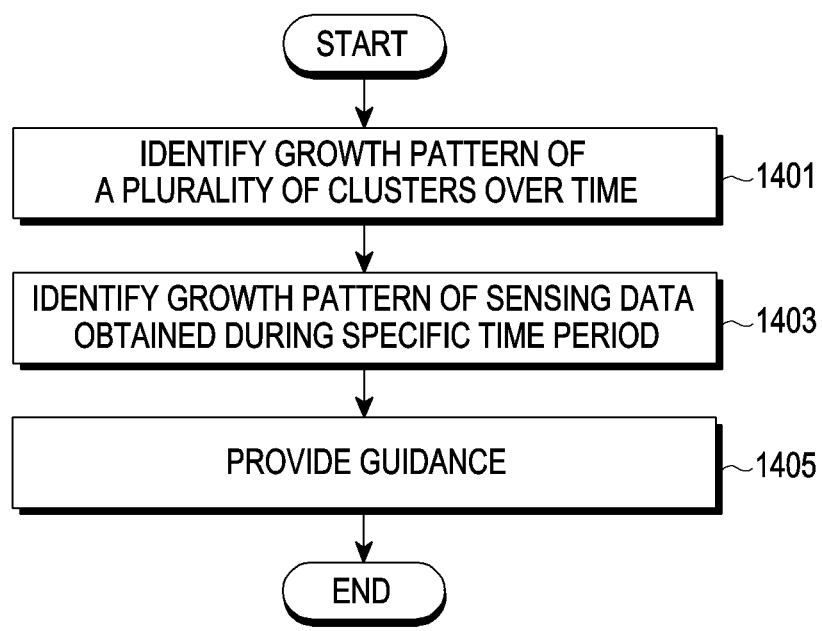
FIG. 14 is a flowchart illustrating an operation of providing guidance by identifying a growth pattern of a plurality of clusters by an electronic device according to certain embodiments.

FIG. 14 is a flowchart illustrating an operation of providing guidance by identifying a growth pattern of a plurality of clusters by an electronic device according to certain embodiments.

Referring to FIG. 14, according to certain embodiments, a first electronic device (for example, the first electronic device 201 of FIG. 2) may identify a growth pattern of a plurality of clusters included in cluster information over time in operation 1401. For example, the first electronic device 201 may identify the growth pattern of the plurality of clusters of existing data by identifying the growth pattern in each unit time.

According to certain embodiments, in operation 1403, the first electronic device 201 may identify a growth pattern of newly obtained sensing data during a specific time period. For example, the first electronic device 201 may obtain a plurality of clusters by clustering the newly obtained sensing data during the specific time period, and identify the growth pattern of the plurality of clusters by monitoring the plurality of clusters in each unit time.

According to certain embodiments, in operation 1405, the first electronic device 201 may provide guidance (or guide information) on activity information about a user. For example, the first electronic device 201 may compare the growth pattern of the plurality of clusters of the sensing data obtained in operation 1403 with the growth pattern of the plurality of clusters of the existing data identified in operation 1401. The first electronic device 201 may provide guidance for a user activity according to the comparison result. For example, the first electronic device 201 may identify whether training (or activities) used for exercise, activities, prescription, and so on of the user matches a growth direction of the clusters, and provide guidance for the training direction. For example, when the growth direction of the newly obtained clusters does not match the growth direction of the existing clusters, the first electronic device 201 may provide guidance indicating correction of the training direction (or activity direction). Alternatively, the first electronic device 201 may provide guidance indicating that the training direction is to be maintained when the growth direction of the newly obtained clusters matches the growth direction of the existing clusters.

Figure 15A:
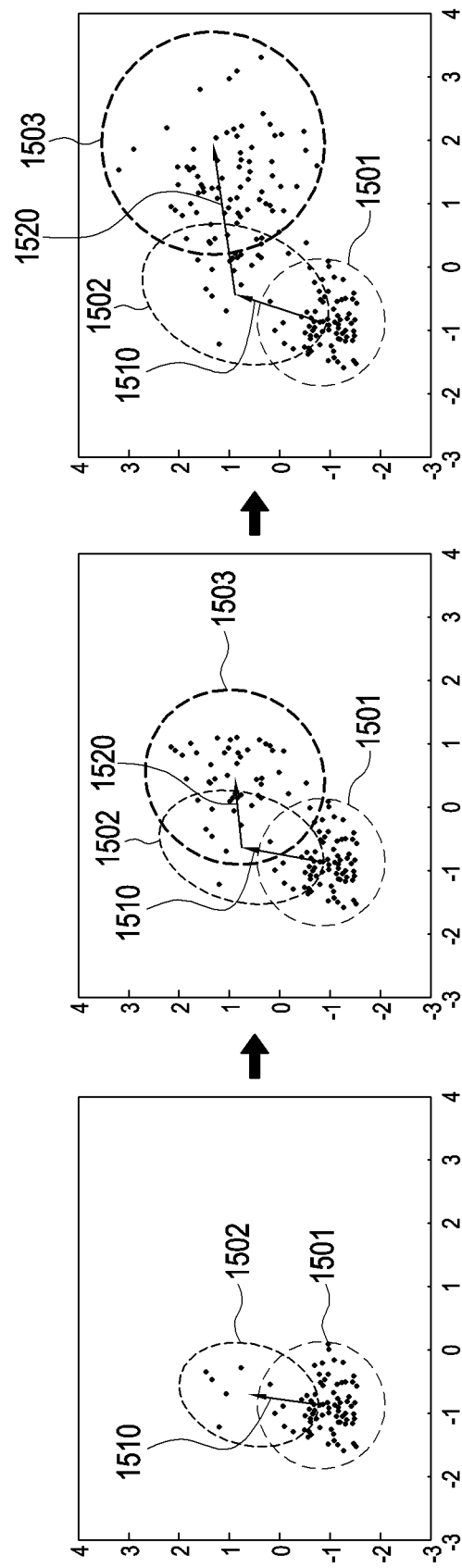
FIGS. 15A and 15B are diagrams illustrating an operation of providing guidance by identifying a growth pattern of a plurality of clusters by an electronic device according to certain embodiments.
Figure 15B:
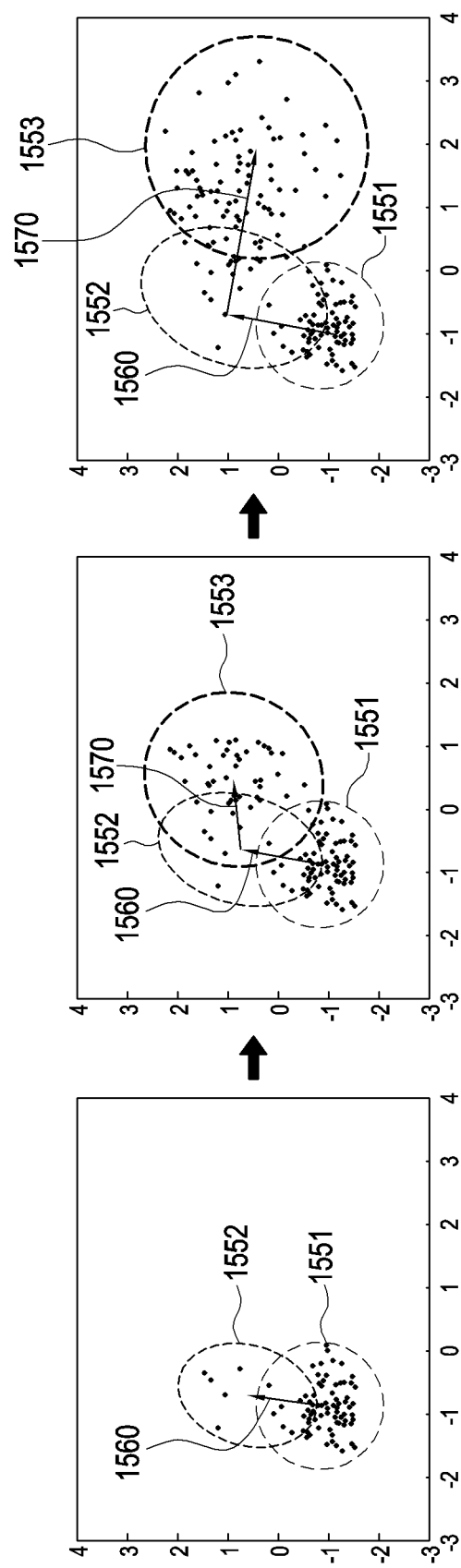

FIGS. 15A and 15B are diagrams referred to for describing an operation of identifying a growth pattern of a plurality of clusters and providing guidance by an electronic device according to certain embodiments.

Referring to FIG. 15A, a first electronic device (for example, the first electronic device 201 of FIG. 2) may obtain cluster information of data related to existing user activities. The first electronic device 201 may identify a change in a plurality of clusters 1501, 1502, and 1503 in each unit time to identify the growth pattern of the plurality of clusters 1501, 1502, and 1503. The first electronic device 201 may identify the growth pattern of the plurality of clusters 1501, 1502, and 1503 using vector values of straight lines connecting the centers of the plurality of clusters 1501, 1502, and 1503. For example, the first electronic device 201 may identify a first vector 1510 connecting the center of the first cluster 1501 to the center of the second cluster 1502 and a second vector 1520 connecting the centers of the first cluster 1501, the second cluster 1502, and the third cluster 1503. The first electronic device 201 may identify the growth pattern of the plurality of clusters based on changes in the first vector 1510 and the second vector 1520 in each unit time.

Referring to FIG. 15B, a first electronic device (for example, the first electronic device 201 of FIG. 2) may obtain cluster information about newly obtained sensing data. The first electronic device 201 may identify a change in a plurality of clusters 1551, 1552, and 1553 in each unit time to identify the growth pattern of the plurality of clusters 1551, 1552, and 1553. For example, the first electronic device 201 may identify a first vector 1560 connecting the center of the first cluster 15551 to the center of the second cluster 1552 and a second vector 170 connecting the center of the second cluster 1552 to the center of the third cluster 1553. The first electronic device 201 may identify the growth pattern of the plurality of clusters based on changes in the first vector 1560 and the second vector 1570 in each unit time.

According to certain embodiments, the first electronic device 201 may compare the growth pattern of the plurality of clusters of the newly obtained sensing data with the growth pattern of the plurality of clusters of the existing data. For example, the first electronic device 201 may compare the first vector 1510 and the second vector 1520 of the existing data with the first vector 1560 and the second vector 1570 of the new sensing data, respectively. The first electronic device 201 may identify that the second vector 1520 of the existing data is different from the second vector 1570 of the new data. The first electronic device 201 may provide guidance on a user activity according to the comparison result.

While the operation of identifying the growth pattern of clusters is described in FIGS. 14, 15A, and 15B as performed by the first electronic device 201, the present disclosure is not limited thereto. For example, at least a part of the operation of identifying the growth pattern of clusters and providing guidance may be performed by the server 208.

According to certain embodiments, an electronic device comprises a communication module; a plurality of sensors and configured to obtain sensing data; at least one processor operatively connected to the plurality of sensors and the communication module; and a memory operatively connected to the at least one processor, wherein the memory stores instructions that, when executed, cause the at least one processor to perform a plurality of operations comprising: transmitting the sensing data to a server through the communication module; receiving, from the server, information on a similarity between the sensing data and a first cluster among a plurality of clusters clustering data related to user activities, through the communication module, wherein the similarity is identified based on a center similarity score between the sensing data and the first cluster, a score that is a function of a variance of the first cluster, a score that is a function a distance between the first cluster and other clusters, and an intersection score between the first cluster and a second cluster adjacent to the first cluster; and executing a function corresponding to the sensing data based on the similarity.

According to certain embodiments, the similarity is set to be inversely proportional to the center similarity score and the intersection score and proportional to the score that is the function of the variance of the first cluster and the score that is the function of the distance between the first cluster and the second cluster.

According to certain embodiments, the first cluster is a cluster close to the sensing data or a cluster including the sensing data.

According to certain embodiments, the center similarity score includes a value corresponding to an angle between a center vector of the first cluster and a vector corresponding to the sensing data; the intersection score includes a value corresponding to an overlap area ratio between the first cluster and the second cluster; the score that is the function of the variance of the first cluster includes a value corresponding to a distance between data included in the first cluster and the center of the first cluster; and the score that is the function of the distance between the first cluster and the second cluster includes values corresponding to distances between the first cluster and the other clusters among the plurality of clusters.

According to certain embodiments, the plurality of operations further comprise identifying a reliability of the sensing data based on the similarity.

According to certain embodiments, the plurality of operations further comprise discarding the sensing data, when the reliability is less than a predetermined value.

According to certain embodiments, the plurality of operations further comprise requesting user authentication, when the reliability is less than a predetermined value.

According to certain embodiments, the plurality of operations further comprise providing an alarm by at least one of a visual means, an auditory means, or a tactile means, when the reliability is less than a predetermined value.

According to certain embodiments, an electronic device comprises: a plurality of sensors; at least one processor operatively connected to the plurality of sensors; and a memory operatively connected to the at least one processor and configured to store information about a plurality of clusters obtained by clustering data related to user activities, wherein the memory stores instructions which, when executed, cause the at least one processor to perform a plurality of operations comprising: obtaining sensing data through the sensor module; identifying a similarity between the sensing data and a first cluster among the plurality of clusters, wherein the similarity is identified based on a center similarity score between the sensing data and the first cluster, a score that is a function of a variance of the first cluster, a score that is a function of a measure of a distance between the first cluster and a second cluster adjacent to the first cluster, and an intersection score between the first cluster and the second cluster; and executing a function corresponding to the sensing data based on the similarity.

According to certain embodiments, the electronic device further comprises a communication module, and wherein the plurality of operations further comprise receiving information about the plurality of clusters from a server through the communication module.

According to certain embodiments, the plurality of operations further comprise obtaining the information about the plurality of clusters by clustering the data related to the user activities.

According to certain embodiments, the similarity is set to be inversely proportional to the center similarity score and the intersection score and proportional to the score that is the function of the variance of the first cluster and the score that is the function of the measure of the distance between the first cluster and the second cluster.

According to certain embodiments, the plurality of operations further comprise determining a cluster close to the sensing data or a cluster including the sensing data as the first cluster.

According to certain embodiments, the center similarity score includes a value corresponding to an angle between a center vector of the first cluster and a vector corresponding to the sensing data; the intersection score includes a value corresponding to an overlap area ratio between the first cluster and the second cluster; the score that is the function of the variance of the first cluster includes a value corresponding to a distance between data included in the first cluster and the center of the first cluster; and the score that is the function of the measure of the distance between the first cluster and the second cluster includes values corresponding to distances between the first cluster and other clusters among the plurality of clusters.

According to certain embodiments, the plurality of operations further comprise providing an alarm by at least one of a visual means, an auditory means, or a tactile means, when a reliability of the sensing data is less than a predetermined value.

According to certain embodiments, an electronic device comprises a plurality of sensors; at least one processor operatively connected to the sensor module; and a memory operatively connected to the processor, wherein the memory stores instructions which, when executed, cause the at least one processor to perform a plurality of operations comprising: obtaining a plurality of sensing data through the plurality of sensors; identifying activity information based on first sensing data among the of sensing data, wherein the other sensing data except for the first sensing data is not used to identify the activity information; identifying a similarity between the sensing data and a plurality of clusters related to the sensing data; and identifying a reliability of the activity information based on the similarity.

According to certain embodiments, wherein the similarity is identified based on a center similarity score between the sensing data and a first cluster among the plurality of clusters, a score that is a function of the variance of the first cluster, a score that is a function of a measure of a distance between the first cluster and a second cluster adjacent to the first cluster, and an intersection score between the first cluster and the second cluster.

According to certain embodiments, the plurality of operations further comprise identifying the similarity through a server.

According to certain embodiments, the plurality of operations further comprise determining whether to use the activity information based on the reliability.

According to certain embodiments, the plurality of operations further comprise: identifying a growth pattern of the plurality of clusters over time; and providing information about the activity information according to a result of comparison between the sensing data and the growth pattern.]

As is apparent from the foregoing description, an electronic device according to certain embodiments of the present disclosure may overcome a reliability problem in newly obtained user activity data by comparing a plurality of clusters obtained by clustering existing user activity data with the newly obtained user activity data.

Each of the afore-described components of the electronic device may include one or more components, and the name of the corresponding components may vary according to the type of the electronic device. In certain embodiments, the electronic device may be configured to include at least one of the above-described components. Some components may be omitted in or other components may be added to the electronic device. In addition, some of the components of the electronic device according to certain embodiments may be combined into a single entity, so that functions of the corresponding components before the combination may be performed in the same manner.

The embodiments disclosed herein are provided to describe and help the understanding of the technical content, not limiting the scope of the present disclosure. Therefore, the scope of the present disclosure should be interpreted as encompassing all modifications or various other embodiments based on the technical idea of the present disclosure.

What is claimed is:

1. An electronic device comprising:
   a communication module;
   a plurality of sensors;
   at least one processor operatively connected to the plurality of sensors and the communication module; and
   a memory operatively connected to the at least one processor,
   wherein the memory stores instructions that, when executed, cause the electronic device to perform a plurality of operations comprising:
   obtaining, through the plurality of sensors, sensing data related to an activity of a user;
   transmitting the sensing data to a server through the communication module;
   receiving, from the server, information on a similarity between the sensing data and a first cluster among a plurality of clusters clustering data related to user activities, the first cluster comprising a plurality of data points related to the activity, through the communication module, wherein the similarity is identified based on at least one of a center similarity score between the sensing data and the first cluster, a first score that is related to a variance of the plurality of data points of the first cluster, a second score that is related to a distance between the first cluster and other clusters, or an intersection score between the first cluster and a second cluster adjacent to the first cluster; and
   executing a function corresponding to the sensing data based on the similarity,
   wherein the first cluster is a cluster close to the sensing data or a cluster including the sensing data,
   wherein the center similarity score includes a value corresponding to an angle between a center vector of the first cluster and a vector corresponding to the sensing data;
   the intersection score includes a value corresponding to an overlap area ratio between the first cluster and the second cluster;
   the first score includes a value corresponding to a distance between each of the plurality of data points included in the first cluster and a center of the first cluster; and
   the second score includes values corresponding to distances between the first cluster and the other clusters among the plurality of clusters.

2. The electronic device of claim 1, wherein the similarity is set to be inversely proportional to the center similarity score and the intersection score and proportional to the first score that is related to the variance of the first cluster and the second score that is related to the distance between the first cluster and the second cluster.

3. The electronic device of claim 1, the plurality of operations further comprises identifying a reliability of the sensing data based on the similarity.

4. The electronic device of claim 3, the plurality of operations further comprises discarding the sensing data, when the reliability is less than a predetermined value.

5. The electronic device of claim 3, the plurality of operations further comprises requesting user authentication, when the reliability is less than a predetermined value.

6. The electronic device of claim 3, wherein the plurality of operations further comprises providing an alarm by at least one of a visual means, an auditory means, or a tactile means, when the reliability is less than a predetermined value.

7. An electronic device comprising:
   a plurality of sensors;
   at least one processor operatively connected to the plurality of sensors; and
   a memory operatively connected to the at least one processor and configured to store information about a plurality of clusters obtained by clustering data related to user activities,
   wherein the memory stores instructions which, when executed, cause the electronic device to perform a plurality of operations comprising:
   obtaining, through the plurality of sensors, sensing data related to an activity of a user;
   identifying a similarity between the sensing data and a first cluster among the plurality of clusters, the first cluster comprising a plurality of data points related to the activity, wherein the similarity is identified based on at least one of a center similarity score between the sensing data and the first cluster, a first score that is related to a variance of the plurality of data points of the first cluster, a second score that is related to a measure of a distance between the first cluster and a second cluster adjacent to the first cluster, or an intersection score between the first cluster and the second cluster; and
   executing a function corresponding to the sensing data based on the similarity,
   wherein the first cluster is a cluster close to the sensing data or a cluster including the sensing data, wherein the center similarity score includes a value corresponding to an angle between a center vector of the first cluster and a vector corresponding to the sensing data;

the intersection score includes a value corresponding to an overlap area ratio between the first cluster and the second cluster;

the first score includes a value corresponding to a distance between each of the plurality of data points included in the first cluster and a center of the first cluster; and the second score includes values corresponding to distances between the first cluster and other clusters among the plurality of clusters.

8. The electronic device of claim 7, further comprising a communication module,
wherein the plurality of operations further comprises receiving information about the plurality of clusters from a server through the communication module.

9. The electronic device of claim 7, wherein the plurality of operations further comprises obtaining the information about the plurality of clusters by clustering the sensing data.

10. The electronic device of claim 7, wherein the similarity is set to be inversely proportional to the center similarity score and the intersection score and proportional to the first score that is related to the variance of the first cluster and the second score that is related to the measure of the distance between the first cluster and the second cluster.

11. The electronic device of claim 7, wherein the plurality of operations further comprises providing an alarm by at least one of a visual means, an auditory means, or a tactile means, when a reliability of the sensing data is less than a predetermined value.

12. An electronic device comprising:
a plurality of sensors;
at least one processor operatively connected to the plurality of sensors; and
a memory operatively connected to the at least one processor,
wherein the memory stores instructions which, when executed, cause the electronic device to perform a plurality of operations comprising:
obtaining a plurality of sensing data through the plurality of sensors;
identifying activity information related to an activity of a user based on first sensing data among the plurality of sensing data, wherein other sensing data except for the first sensing data is not used to identify the activity information;
identifying a similarity between the plurality of sensing data and a plurality of clusters related to the plurality of sensing data, wherein the plurality of clusters comprises a first cluster, the first cluster comprising a plurality of data points related to the activity, and wherein the similarity is identified based on at least one of a center similarity score between the plurality of sensing data and a first cluster among the plurality of clusters, a first score that is related to a variance of the plurality of data points of the first cluster, a second score that is related to a measure of a distance between the first cluster and a second cluster adjacent to the first cluster, and an intersection score between the first cluster and the second cluster; and
identifying a reliability of the activity information based on the similarity,
wherein the first cluster is a cluster close to the plurality of sensing data or a cluster including the plurality of sensing data,
wherein the center similarity score includes a value corresponding to an angle between a center vector of the first cluster and a vector corresponding to the plurality of sensing data;
the intersection score includes a value corresponding to an overlap area ratio between the first cluster and the second cluster;
the first score includes a value corresponding to a distance between each of the plurality of data points included in the first cluster and a center of the first cluster; and
the second score includes values corresponding to distances between the first cluster and other clusters among the plurality of clusters.

13. The electronic device of claim 12, wherein the plurality of operations further comprises identifying the similarity through a server.

14. The electronic device of claim 12, wherein the plurality of operations further comprises determining whether to use the activity information based on the reliability.

15. The electronic device of claim 12, wherein the plurality of operations further comprises:
identifying a growth pattern of the plurality of clusters over time; and
providing information about the activity information according to a result of comparison between the plurality of sensing data and the growth pattern.

* * * * *